United States Patent [19]

Kodaka et al.

[11] Patent Number: 5,310,920

[45] Date of Patent: May 10, 1994

[54] N-VINYLIMIDAZOLIDINE DERIVATIVES INSECTICIDES CONTAINING SAME AS AN EFFECTIVE INGREDIENT

[75] Inventors: Kenji Kodaka; Michihiko Nakaya; Katsutoshi Kinoshita; Koichi Ebihara; Hirozumi Matsuno; Shirou Shiraishi; Kazutomi Ohnuma; Ei-ich Yamada, all of Mobara, Japan

[73] Assignee: Mitsui Toatsu Chemicals, Inc., Tokyo, Japan

[21] Appl. No.: 991,051

[22] Filed: Dec. 15, 1992

[30] Foreign Application Priority Data

Dec. 16, 1991 [JP] Japan .................... 3-331781

[51] Int. Cl.$^5$ ................ C07D 401/06; A61K 31/44
[52] U.S. Cl. .................... 514/341; 514/333; 514/338; 514/365; 546/278; 546/256; 546/280; 546/270; 548/205; 548/311.7; 548/331.5
[58] Field of Search ........... 546/256, 278, 280, 270; 548/205; 514/333, 341, 338, 365

[56] References Cited

U.S. PATENT DOCUMENTS

| | | | |
|---|---|---|---|
| 4,742,060 | 5/1988 | Shiokawa et al. | 514/252 |
| 4,845,106 | 7/1989 | Shiokawa et al. | 514/342 |
| 4,880,933 | 11/1989 | Shiokawa et al. | 544/332 |
| 5,001,138 | 3/1991 | Shiokawa et al. | 514/342 |

FOREIGN PATENT DOCUMENTS 0192060 8/1986 European Pat. Off. .
0277317 8/1988 European Pat. Off. .
0285985 10/1988 European Pat. Off. .

*Primary Examiner*—Jane T. Fan
*Attorney, Agent, or Firm*—Millen, White, Zelano & Branigan

[57] ABSTRACT

The present invention relates to novel N-vinylimidazolidine derivatives of the following formula (1), a process for producing them, an insecticide containing the derivatives as an effective ingredient, and novel intermediates. The derivatives (1) are useful as agricultural chemicals (particularly, as insecticides) in the fields of agriculture, and the intermediates are useful in various industrial fields, especially as intermediates for agricultural chemicals.

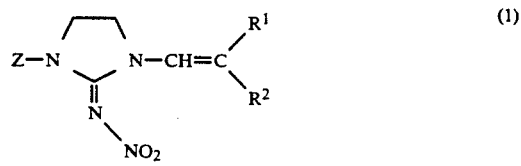

where $R^1$, $R^2$, Z are as defined in the specification.

8 Claims, No Drawings

N-VINYLIMIDAZOLIDINE DERIVATIVES INSECTICIDES CONTAINING SAME AS AN EFFECTIVE INGREDIENT

FIELD OF THE INVENTION

The present invention relates to novel imidazolidine derivatives, their preparation, insecticides containing the derivatives as an effective ingredient, and novel intermediates.

N-vinylimidazolidine derivatives of the present invention are useful as agricultural chemicals (particularly, as insecticides) in the field of agriculture and intermediates of the dervitatives are useful in various industrial fields and particularly as intermediates for agricultural chemicals.

PRIOR ART

Heretofore, a lot of insecticidal compounds having a skeleton of imidazolidine derivatives have been known. A lot of compounds having an imidazolidine skeleton having also been disclosed. For instance, USP 4,742,060 describes imidazolidine derivatives of the following formula in which R represents an optionally halogen-substituted alkenyl group having from 2 to 3 carbon atoms and it is disclosed that the derivatives have an insecticidal activity, concretely illustrating 1-(2-chloropyridin-5-ylmethyl)-2-nitroimino-3-allylimidazolidine (R is allyl).

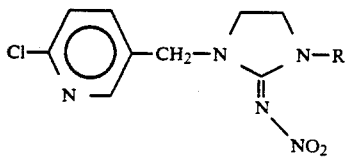

As a method of producing the derivatives the following reaction scheme is disclosed:

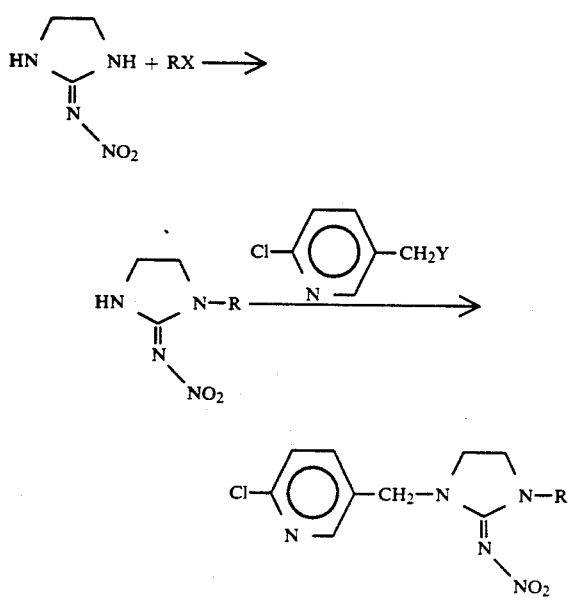

PROBLEMS TO BE SOLVED BY THE INVENTION

Heretofore, a lot of insecticidal compounds having an imidazolidine skeleton have been known. However, in general, these compounds have various problems for use as an agricultural chemical, as they have high acute toxicity and remain in crops for a long period of time. In addition, they have high solubility in water so that when they are used as a spraying powder, they cause a problem of environmental pollution of ground water and rivers. Due to the prospect that this environmental problem will be much severe in the future, agricultural chemicals which are non-toxic, which are easily decomposed in the environment as opposed remaining therein and which ,do not contaminate rivers are in high demand. Therefore the present inventors have studied production of N-vinylimidazolidine derivatives and their bological activity. As a result, they have succeeded in the production of novel N-vinylimidazolidine derivatives which are not described in the known literature and additionally have found that the derivatives have an extremely excellent insecticidal activity.

Accordingly, it is an object of the present invention to provide novel N-vinylimidazolidine derivatives which are free from drawbacks of the abovementioned known imidazolidine derivatives, a simple process for producing the derivatives, high-activity insecticides containing the derivatives as an effective ingredient, and novel intermediates for production of the novel N-vinylimidazolidine derivatives.

SUMMARY OF THE INVENTION

The present inventors earnestly investigated so as to solve the above-mentioned problems and, as a result, have found that novel N-vinylimidazolidine derivatives of the formula (1) have an excellent insecticidal activity. On the basis of the finding, they have completed the present invention.

According to the present invention, there are provided N-vinylimidazolidine derivatives of a formula (1):

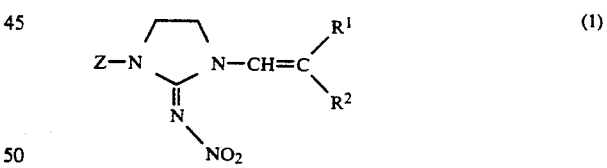

where $R^1$ represents a hydrogen atom, a phenyl group, or an alkyl group having from 1 to 4 carbon atoms; $R^2$ represents a hydrogen atom, a phenoxy group, a benzyl group, a phenyl group, an aldehyde group, a 2-chloropyridin-5-ylmethyl group, a benzoylamino group, an alkyl group having from 1 to 18 carbon atoms, an alkoxy group having from 1 to 4 carbon atoms, an alkylthio group having from 1 to 4 carbon atoms, a phenyl group substituted by halogen atom(s), a phenyl group substituted by cyano group(s), a phenyl group substituted by phenyl group(s), a phenyl group substituted by benzoyl group(s), a phenyl group substituted by methylenedioxy group(s), a phenyl group substituted by alkyl group(s) having from 1 to 4 carbon atoms, a phenyl group substituted by alkoxy group(s) having from 1 to 4 carbon atoms, a phenyl group substituted by alkylthio group(s) having from 1 to 4 carbon atoms, a phenyl group substituted by haloalkyl group(s) having from 1 to 4 carbon atoms, or a phenyl group substituted by haloalkoxy group(s) having from 1 to 4 carbon atoms; and Z represents a 2-chloropyridin-5-ylmethyl group or a 2-chlorothiazol-5ylmethyl group; and a process of producing compounds of the formula (1) by reacting a compound of a formula (2):

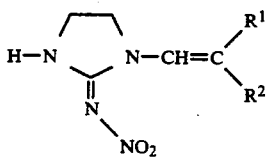 (2)

where $R^1$ and $R^2$ have the same meanings as mentioned above, and a compound of a formula (3):

Z—X     (3)

where Z has the same meaning as mentioned above; and X represents a chlorine atom or a bromin atom; and an insecticide containing a compound of the formula (1) as an effective ingredient; and N-vinylimidazolidine derivatives of the formula (2); and a process of producing N-vinylimidazolidine derivatives of the formula (2) by reacting a compound of a formula (4):

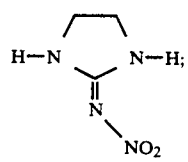 (4)

where $R^1$ and $R^2$ have the same meanings as mentioned above, and a compound of a formula (5):

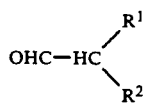 (5)

and a process of producing N-vinylimidazolidine derivatives of the formula (2) by reacting a compound of a formula (6):

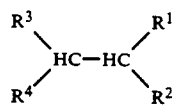 (6)

where $R^1$ and $R^2$ have the same meanings as mentioned above; and R3 and R4 each represents an alkoxy group, an alkylthio group, an alkylsulfoxido group, a phenoxy group, a phenylthio group, or a phenylsulfoxido group, or R3 and R4 are bonded to each other to form an alkylenedioxy group or an alkylenedithio group, and a compound of the formula (5); and a process of producing N-vinylimidazolidine derivatives of the formula (2):

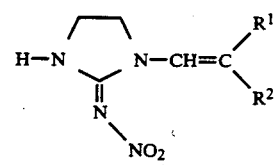 (2)

where $R^1$ and $R^2$ have the same meanings as mentioned above, by reacting a compound of a formula (7):

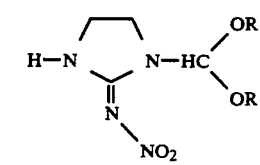 (7)

where R represents a lower alkyl group, and a compound of a formula (8):

 (8)

where $R^1$ and $R^2$ have the same, meanings, as mentioned above.

DETAILED DESCRIPTION OF THE INVENTION briefly the present invention provides novel N-vinylimidazolidine derivatives of the formula (1):

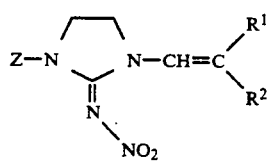 (1)

where $R^1$ and $R^2$ have the same meanings as mentioned above, a process of producing them, an insecticide containing them as an effective ingredient, novel intermediates, which are for producing the compounds (1), of the formula (2):

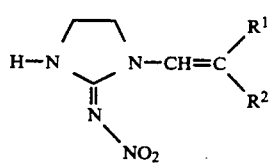 (2)

where $R^1$ and $R^2$ have the same meanings as mentioned above, and processes of producing the intermediates.

Specific examples of the alkyl group having from 1 to 18 carbon atoms for $R^1$ and $R^2$ in the above-mentioned formulae include a methyl group, as ethyl group, an n-propyl group, an iso propyl group, an n-butyl group, an iso-butyl group, a sec-butyl group, a tert-butyl group, an n-pentyl group, an n-hexyl group, an n-octyl group, an n-decyl group and an n-octadecyl group; the alkoxy group having from 1 to 4 carbon atoms include a methoxy group, an ethoxy group, an n-propoxy group, an iso-propoxy group, an n-butoxy group, an iso-butoxy group and a sec-butoxy group; the alkylthio group having from 1 to 4 carbon atoms include a methylthio group, an ethylthio group, an n-propylthio group, an isopropylthio group and an n-butylthio group.

As substituents of the substituted phenyl group, mentioned are, for example, a alkyl group having from 1 to 4 carbon atoms such as a methyl group, an ethyl group, a propyl group, an iso-propyl group and a t-butyl group; a halogen atom such as a fluorine atom, a chlorine atom, a bromine atom and an iodine atom; an alkoxy group having from 1 to 4 carbon atoms such as a methoxy group, an ethoxy group, an n-propoxy group, an iso-propoxy group, an n-butoxy group, an iso-butoxy group and a sec-butoxy group; an alkylthio group having from 1 to 4 carbon atoms such as a methylthio group, an ethylthio group, an n-propylthio group, an iso-propylthio group and an n-butylthio group; a haloalkoxy group having from 1 to 4 carbon atoms such as a difluoromethoxy group, a trifluoromethoxy group, a difluorochloromethoxy group, a difluorobromomethoxy group, a chloromethoxy group, a dichloromethoxy group, a trichloromethoxy group, a bromomethoxy group, a 2-chloroethoxy group, a 2bromoethoxy group, a 1,1-difluoro-2,2-dichloroethoxy group, a 1,1,2,2-tetrafluoroethoxy group, a 2,2,2-trifluoroethoxy group, a 1,1-dibromo-2,2,2-trifluoroethoxy group, a 2,2-dichloroethoxy group, a 2,2,2-trichloroethoxy group, a 1,2-dichloroethoxy group, a 3-chloropropoxy group, a 3-bromopropoxy group, a 4-chlorobutoxy group and a 4-bromobutoxy group; and a haloalkyl group having from 1 to 4 carbon atoms such as a trifluoromethyl group, a 2,2,2-trifluoroethyl group, perfluorobutyl group, a chloromethyl group, a dichloromethyl group, a trichloromethyl group, a 2-chloroethyl group and a bromomethyl group. The substituted phenyl group includes a di-substituted one.

Compounds of the formula (1) may be produced in accordance with the following reaction scheme (1):

Reaction Scheme (1):

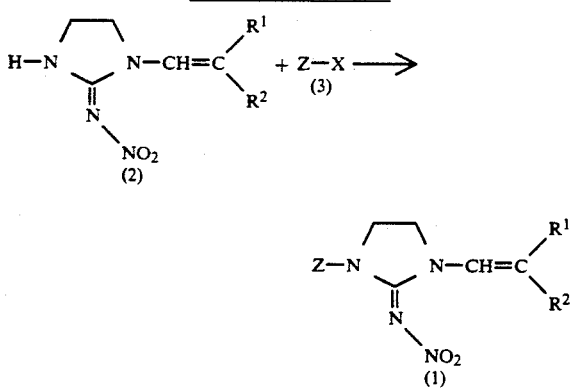

where $R^1$, $R^2$, Z and X have the same meanings as mentioned above.

Compounds (1) and intermediates (2) both include E- and Z-isomers.

Compounds of the formula (1) may be produced with ease by reacting an N-vinylimidazolidine derivative of the formula (2) and a 2-chloropyridin-5-ylmethyl halide or 2-chlorothiazol-5-ylmethyl halide of the formula (3) in the presence of a deacidifying agent in various solvents.

Examples of the deacidifying agent include alkali metal hydroxides such as sodium hydroxide, potassium hydroxide and the like; alkaline earth metal hydroxides such as magnesium hydroxide, calcium hydroxide and the like; alkali metal hydrides such as sodium hydride, potassium hydride and the like; alkali metal alcoholates such as sodium methylate, sodium ethylate and the like; alkali metal oxides such as sodium oxide and the like; carbonates such as sodium carbonate, potassium carbonate and the like; hydrogencarbonates such as sodium hydrogencarbonate, potassium hydrogencarbonate and the like; hydrogensulfates such as sodium hydrogensulfate, potassium hydrogensulfate and the like; phosphates such as trisodium phosphate, disodium phosphate and the like; acetates such as sodium acetate, potassium acetate and the like; organic bases such as triethylamine, DBU, DIMAP and the like; and butyl lithium, sodium amide, and the like.

The solvents may include not only water but also aromatic hydrocarbons such as benzene, toluene, xylene and the like; aliphatic hydrocarbons such as hexane, heptane, petroleum benzine and the like; aprotic polar solvents such as dimethylformamide, dimethylacetamide, dimethylsulfoxide, 1,3-dimethyl-2-imidazolidinone, 1-methyl-2-pyrrolidinone and the like; ethers such as ethyl ether, diisopropyl ether, 1,2-dimethoxyethane, tetrahydrofuran, dioxane and the like; nitriles such as acetonitrile, propionitrile and the like; ketones such as acetone, diisopropyl ketone and the like; esters such as methyl acetate, ethyl acetate, ethyl propionate and the like; and alcohols such as methanol, ethanol, propanol, 2-ethylhexyl alcohol and the like.

When phase transfer catalyst such as tetrabutylammonium bromide, triethylbenzylammonium chloride and the like are used, the intended imidazolidine derivatives can be obtained in high yield.

The reaction temperature and the reaction time can be varied over wide ranges. In general, the reaction temperature is in the range of from −20° to 100° C., preferably from 0° to 100° C.; and the reaction time is in the range of from 0.01 to 30 hours, preferably from 0.1 to 15 hours.

Though not always necessary, substituent(s) of a compound of the formula (2) may be protected with so-called protective group(s) to produce a derivative of the intended compound (1), which is then deprotected to obtain the N-vinylimidazolidine derivative (1).

In the preceding reaction scheme, the starting compound of the formula (2):

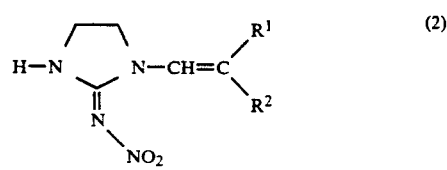

may be produced in accordance with the following reaction scheme (2):

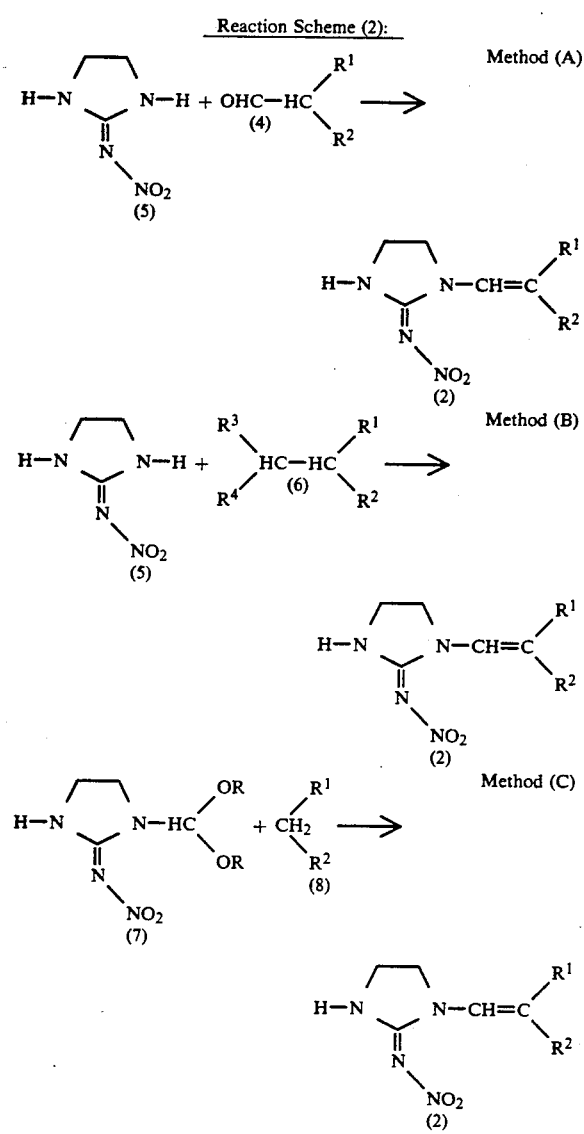

where $R^1$, $R^2$, $R^3$, $R^4$ and R have the same meanings as mentioned above.

Precisely, compounds of the formula (2) may be produced with ease and in high yield by reacting a 2-nitroiminoimidazolidine of the formula (5) and an aldehyde of the formula (4) or an aldehyde homologue of the formula (6). They may also be produced with ease and in high yield by reacting a 2-nitroimino-N-dialkoxymethylimidazolidine of the formula (7) and an active methylene containing compound of the formula (8). In this connection, it is to be specifically noted that compounds of the formula (2) of the present invention could not be produced by the method described in U.S. Pat. No. 4,742,060.

Therefore, compounds of the formula (2) are novel compounds which have first been produced by the present inventors, and the reaction of itself of producing them is also a novel reaction which has first been found out by them.

Method (A) through Method (C) for producing compounds of the formula (2) of the present invention will be explained in detail hereunder.

Method (A)

The reaction may be effected in the absence of a solvent or in a solvent. As the solvent, usable are, for example, alcohols such as methanol, ethanol, propanol and the like; aromatic hydrocarbons such as benzene, toluene, xylene and the like; halogeated hydrocarbons such as chloroform, 1,2-dichloroethane and the like; aprotic polar solvents such as dimethylformamide, dimethylacetamide, dimethylsulfoxide, 1,3-dimehtyl-2-imidazolidinone, 1-methyl-2-pyrrolidinone and the like; ethers such as ethyl ether, diisopropyl ether, 1,2-dimethoxyethane, tetrahydrofuran, dioxane and the like; nitrile such as acetonitrile, propionitrile and the like; and ketones such as acetone, diisopropyl ketone and the like.

Though not always necessary, a catalyst may be used for the reaction, which includes, for example, mineral acids such as sulfuric acid, hydrochloric acid, phosphoric acid, nitric acid and the like; sulfonic acids such as p-toluenesulfonic acid, methanesulfonic acid, trifluoromethanesulfonic acid and the like; carboxylic acids such as acetic acid, benzoic acid., formic acid and the like; Lewis acids such as aluminum chloride, tin tetrachloride, zinc chloride, boron trifluoride, titanium tetrachloride and the like; ammonium salts such as pyridine hydrochloride, tetrametylammonium chloride and the like; hydrogensulfates such as sodium hydrogensulfate, potassium hydrogensulfate and the like; hydrogencarbonates such as sodium hydrogencarbonate, potassium hydrogencarbonate and the like; acidic or basic oxides such as zirconium oxide, silica gel, alumina and the like; acidic gas such as sulfurous acid gas, carbon dioxide and the like; and phenols, and the like.

The reaction temperature and the reaction time can be varied over wide ranges. In general, the reaction temperature is in the range of from $-80°$ to $300°$ C., preferably from $-30°$ to $200°$ C.

The reaction is effected generally under a normal pressure condition but may also be effected under an elevated pressure.

The reaction time is in the range of from 0.001 to 30 hours, preferably from 0.01 to 20 hours.

The amount of the aldehyde derivative (4) to be used may be from 0.1 to 30 mols, economically from 0.3 to 10.0 mols, per mol of the 2-nitroiminoimidazolidine (5).

Compounds of the formula (5) may be produced by reaction of ethylenediamine or its hydrochloride and nitroguanidine (literature for the production method: J. Am. Chem. Soc., 70, 430 (1948)).

Method (B)

Compounds of the formula (2) may be produced with ease and in high yield by reaction of a compound of the formula (6) and a 2-nitroiminoimidazolidine derivative of the formula (5).

The reaction may be effected in the absence of a solvent or in a solvent. As the solvent, usable are, for example, aromatic hydrocarbons such as benzene, toluene, xylene and the like; halogenated hydrocarbons such as chloroform, 1,2-dichloroethane and the like; aprotic polar solvents such as dimethylformamide, dimethylacetamide, dimethylsulfoxide, 1,3-dimethyl−2-imidazolidinone, 1-methyl−2-pyrrolidinone and the like; ethers such as ethyl ether, diisopropyl ether, 1,2-dimethoxyethane, tetrahydrofuran, dioxane and the like; nitriles such as acetonitrile propionitrile and the like; ketones such as acetone, diisopropyl ketone and the like; and alcohols such as methanol, ethanol, propanol and the like.

Though not always necessary, a catalyst may be used for the reaction, which includes, for example, mineral acids such as sulfuric acid, hydrochloric acid, phosphoric acid, nitric acid and the like; sulfonic acids such as p-toluenesulfonic acid, methanesulfonic acid, trifluoromethanesulfonic acid and the like; carboxylic acids such as acetic acid, benzoic acid, formic acid and the like; Lewis acids such as aluminium chloride, tin tetrachloride, zinc chloride, boron trifluoride, titanium tetrachloride and the like; ammonium salts such as pyridine hydrochloride, tetramethylammonium chloride and the like; acidic or basic oxides such as zirconium oxide, silica gel, alumina and the like; hydrogensulfates such as sodium hydrogensulfate, potassium hydrogensulfate and the like; hydrogencarbonates such as sodium hydrogencarbonate, potassium hydrogencarbonate and the like; acidic ga such as sulfurous acid gas, carbon dioxide and the like; and phenols, and the like.

The reaction temperature and the reaction time can be varied over wide ranges. In general, the reaction temperature is in the range of from −80° to 300° C., preferably from −30° to 200° C.

The reaction is effected generally under a normal pressure condition but may also be effected under an elevated pressure.

The reaction time is in the range of from 0.001 to 30 hours, preferably from 0.01 to 20 hours.

The amount of the ethane derivative (6) to be used may be 1.0 mol or more per mol of the 2-nitroiminoimidazolidine (5) with no limitation of the uppermost limit thereof. From the economical viewpoint, it is preferably from 0.3 to 10.0 mols per mol of the 2-nitroguanidine (5).

Compounds of the formula (6) may also be obtained by acetalization of an aldehyde of the formula (4) or by reaction of a Grignard reagent and an orthoformate. They may also be obtained by reaction of a methyl methylsulfinylmethylsulfide and an alkyl halide or aryl halide (literatures for the production methods: Journal of Organic Synthetic Chemical Association, Vol. 37, No. 11 (1979); General Logic of Chemistry, No. 19, 75-96 (1978); Tetrahedron Letters, No. 34, 3151-3154 (1974); Tetrahedron Letters, No. 26, 2681-2684 (1972)).

Method (C)

Compounds of the formula (2) may be produced with ease and in high yield by reaction of an aldehyde homologue of the formula (7) and an active methylene-containing compound of the formula (8).

The reaction temperature and the reaction time can be varied over wide ranges. In general, the reaction temperature is in the range of from −80° to 300° C., preferably from −30° to 200° C. The reaction time is in the range of from 0.001 to 30 hours, preferably from 0.01 to 20 hours. The amount of the active methylene containing compound to be used may be 1.0 mol or more per mol of the dialkoxymethylimidazolidine derivative (7) with no limitation of the uppermost limit thereof. From the economical viewpoint, it is preferably from 0.3 to 10.0 mols per mol of the derivative (7).

Alkoxymethylimidazolidine derivatives of the formula (7) may be produced by reaction of an imidazolidine derivative and an orthoformate. The reaction may be effected in the absence of a solvent or in a solvent. As the solvent, usable are, for example, aprotic polar solvents such as dimethylformamide, dimethylsulfoxide, 1,3-dimethyl−2-imidazolidinone and the like. The reaction temperature is in the ran9e of from 50° to 200° C.; and the reaction time is in the ran9e of from 0.5 to 15 hours. The amount of the orthoformate to be used is preferably from 1 to 10 mols per mol of the imidazolidine derivative (5).

Compounds of the formula (7) include tautomers of the following formula (3):

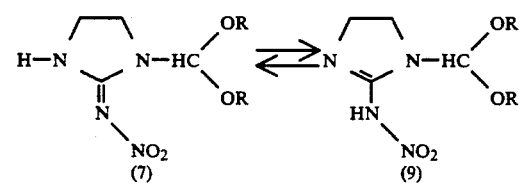

where all R's have the same meanings as above.

On the other hand, 2-chloropyridin−5-ylmethyl halides of the formula (3) and 2-chloro-5 -chloromethylthiaozle are known compounds and can be produced by known methods (literatures for the production method: J. Heterocyclic Chem., 16, 333 (1979); J. Med. Chem., 14, 557 (1971)).

The derivatives of the formula (1) according to the invention have great insecticidal activity and can be used as an insecticide. The derivatives of the formula (1) of the invention show a high control effect on harmful insects without involving any phyto-toxicity to cultivated plants.

Insect pests to which the derivatives of the invention can be applied, for instance, include:

LEPIDOPTERA

*Pieris rapae crucivora* Boisduval—Common cabbageworn
*Spodoptera litura* Fabricius—Common cutworm
*Ostrinia furnacalis* Guenee—Oriental corn borer
*Plutella xylostella* Linne—Diamond backmoth
*Chilo suppressalis* Walker—Rice stem borer
*Cnaphalocrocis medinalis* Guenee—Rice leaf roller

HEMIPTERA

*Neuhotettix cincticeps* Uhler—Green rice leafhopper
*Nilaparvata luqens* Stal—Brown rice planthopper
*Laodelphax striatellus* Fallen—Small brown planthopper
*Unaspis yanonensis* Kuwana—Arrowhead scale
*Mvzus persicae* Sulzer—Green peach aphid
*Aphis qossvpii* Glover—Cotton aphid
*Lipaphis pseudobrassicae* Davis—Turnip aphid
*Nezara antennata* Scott—Common green stink bug
*Trialeurodes vaporariorum* Westwood—Greenhouse whitefly

COLEOPTERA

*Cellosobruches chinensis* Linne—Azuki bean weevil
*Sitophilus oryzae* Linne—Rice weevil
*Henosepilachna viqintioctopunctata* Fablicius—28-spotted lady beetle
*Anomala rufocuprea* Motschulsky—Soy bean beetle
*Leptinotarsa decemlineata* Say—Colorado potato beetle
*Lissorhoptrus oryzophilus* Kuschel—Rice water weevil

ORTHOPTERA

*Blattella qermanica* Linne—German cockroach
*Periplaneta americana* Linne—American cockroach

*Gryllotalpa africana palisot* de Beauvois=African mole cricket
*Locusta miqratoria denica* Linne—Asiatic locust
*Reticulitermes speratus* kolbe
*Coptatermes formosanus* Shiraki—Formosan subleronean termite

DIPTERA

*Musca domestica vicina* Macuart—House fly
*Aedes aegypti* Linne—Yellow fever mosquito
*Culex pipens pallens*—Coquillett
*Culex tritaeniorhyneus*—Giles The compounds of the invention not only have a higher insecticidal effect of exterminating harmful insects as compared with conventional imidazolidine skeleton-containing compounds but also have an extremely low toxicity and therefore may be used safely in all sites. In addition, since the compounds of the invention may rapidly be decomposed by light or the like in the natural environment they hardly remain in crops. Further, the water solubility of the compounds is low so that they hardly dissolve out into ground water or rivers. In producing the compounds of the invention, formation of by-products is extremely small and the compounds may be produced with ease. They are therefore industrially advantageous.

Where the compounds of the formula (1) of the invention is actually applied, they may be used singly without addition of any other ingredient. However, it is usual to formulate them with carriers in order for ease of application as a Reference Chemical.

For preparation of the compounds of the invention, no specific requirement is not necessary to formulate them into various preparations. For example, they may be formulated as emulsons, wettable powders, dusts, granules, fine powders, oils, aerosols, poisonous feeds and the like, according to the procedures of preparing general agricultural chemicals well known in the art.

The term "carrier" used herein is intended to mean synthetic or natural, organic or inorganic materials which assist the effective ingredient to arrive at sites or portions to be treated and which are formulated in order to make easy storage, transport and handling of the effective compound.

Appropriate solid carriers include, for example, clays such as montomorilonite, kaolinite and the like, inorganic substances such as diatomaceous earth, white clay, talc, vermiculite, gypsum, calcium carbonate, silica gel, ammonium sulfate and the like, plant organic substances such as soybean flour, saw dust, wheat flour and the like, and urea.

Suitable liquid carriers include, for example, aromatic hydrocarbons such as toluene, xylene, cumene and the like, paraffin hydrocarbons such as kerosene, mineral oils and the like, ketones such as acetone, methyl ethyl ketone, cyclohexanone and the like, ethers such as dioxane, tetrahydrofuran and the like, glymes such as ethylene glycol dimethyl ether, ethylene glycol diethyl ether and the like, alcohols such as methanol, ethanol, propanol, ethylene glycol and the like; phthalates such as dioctyl phthalate and the like, and dimethylformamide, dimethylsulfoxide, water, and the like.

In order to reinforce the efficacy of the compounds of the formula (1) of the invention, the following adjuvants may be used singly or in combination, depending on the type of preparation, the manner of application and the purpose.

For the purpose of emulsification, dispersion, spreading, wetting, bonding and stabilization, there are used water-soluble salts such as ligninsulfonates, nonionic surface active agents such a alkylbenzene sulfonates, alkylsulfates and the like, lubricants such as calcium stearate, waxes and the like, stabilizers such as isopropoxy hydrogenphosphates, and methyl cellulose, carboxymethyl cellulose, casein, gum arabi and the like. It should be noted that the adjuvants are not limited to those mentioned above and other adjuvants ordinarily used for this purposes may also be used.

The compounds of the formula (1) of the invention may develop better insecticidal activity when used in combination of two or more. If other physiologically active substances or chemicals are used in combination, multi-purpose compositions with good efficacy can be prepared with the possibility of developing a synergistic effect. Examples of such physiologically active substances include: synthetic pyrethroid insecticides and various isomers thereof or pyrethrum extracts, such as allethrin, N-(chrysanthemoylmethyl)-3,4,5,6-tetrahydrophthalimide, 5-benzyl- 3-furylmethyl chrysnthemate, 3-phenoxybenzyl chrysanthemate, 5-propargylfurfuryl chrysanthemate and other known cyclopropanecarboxylic acid esters, 3-phenoxybenzyl 2,2-dimethyl- 3-(2,2-dichlorovinyl)-cyclopropane-1-carboxylate, 3-phenoxy-α-cyanobenzyl 2,2-dimethyl- 3-( 2,2-dichlorovinyl)-cyclopropane-1-carboxylate, 3-phenoxy-α-cyanobenzyl, 2,2-dimethyl-3-(2,2-dibromovinyl)-cyclopropane-1-carboxylate, 3-phenoxy-α-cyanobenzyl-α-isopropyl-4-chlorophenylacetate, lesmetrin, cihalotrin, cifurtrin, fenpropatrin, teralometrin, cycloprotrin, furcitrinate, furvalinate and the like; organo-phosphate insecticides such as O,O-diethyl—O-(3-oxo- 2-phenyl-2H-pyridazin-6-yl)phosphorothioate (available from Mitsui Toatsu Chemicals, Inc. under the trade name of Ofunack), O,O-dimethyl O-(2,2-dichlorovinyl)phosphate (DDVP), O,O-dimethyl-O-(3-methyl-4-nitrophenyl)phosphorothioate, diazinone, O,O-dimethyl-O-4-cyanophenylphosphorothioate, O,O-dimethyl-S-[α-(ethoxycarbonyl)benzyl]phosphorodithioate, 2-methoxy-4H-1,3,2-benzodioxaphosphorin-2-sulfide, O,O-diethyl-O-4cyanophenylphosphonothioate, MMP, pyrimifosmethyl, isoxathione, chloropyrifosmethyl, chloropyrifos, ESP, profenofos, malason, dimethoate, thiomethone, ethylthiomethone, forosan, DMTP, prothiofos, sulprofos, pyrachlofos, monochlotofos, CVP, propafos, acephate, DEP, EPN, ethione and the like; carbamate insecticides such as 1-naphthyl N-methylcarbamate (NAC), m-tolyl N-methylcarbamate (MTMC), 2-dimethylamino-5,6-dimethylpyrimidin-4-yl dimethylcarbamate (Pyrimer), 3,4dimethylphenyl N-methylcarbamate, 2-isopropoxyphenyl N-methylcarbamate, MIPC, BPMC, XMC, ethiophencarb, bendaiocarb, carbosulfan, benfuracarb, mesomil, oxamil, thiodicarb and the like; aryl propyl ether insecticides such as 3-phenoxybenzyl 2-(4-chlorophenyl)-2-methyl propyl ether, 3-phenoxy-4-fluorobenzyl 2-(4-chlorophenyl)-2-methylpropyl ether, 3-phenoxybenzyl 2-(4-ethoxyphenyl)-2methylpropyl ether, 3-phenoxy-4-(florobenzyl 2-(4-ethoxyphenyl)-2methylpropyl ether and the like; aromatic alkane insecticides such as 1-(3-phenoxyphenyl)-4-(4-chlorophenyl)-4-methylpentane, 1-(3-phenoxy-4-fluoropehnyl)-4-(4-chlorophenyl)-4-methylpentane, 1-(3-phenoxyphenyl)-4-(4-ethoxyphenyl)-4-methylpentane 1-(3-phenoxy-4-fluorophenyl)-4-(4-ethoxyphenyl)-4-methylpentane and the like; insecticidal natural substances such a nicotine sulfate, polynactine composites, avermectin, mirbemectin and the like; insecticides such as caltap, thicyclam, bensultap, difurbnzulone, chlorofurazulone, tefurbenzulone, bufurophedine, benzoepine and the like; acaricides such as kersene, CPCBS, BPPS, tetradifon, amitrazu, benzomate, phenothiocarb, hexathiazox, fenbutatin oxide, dienochlor, chlofenthedine, phenopyroxymate and the like; and other insecticides, acaricides, fungicides, nematocides, herbicides, plant growth regulators, fertilizers, soil improving materials, molting inhibitors, JH activators, BT agents, microorganisms-derived toxins, natural or synthetic insect hormone disturbing agents, attractants, repellents, insectopathogenic microorganisms and small animals and other agricultural chemicals.

Although the compounds of the formula (1) of the invention are stable to light, heat and oxidation, antioxidants or UV absorbers may be added in appropriate amounts, if necessary, including, for example, phenol derivatives or bisphenol derivatives such as BHT (2,6-di-t-butyl-4-methylphenol), BHA (butylhydroxyanisole) and the like, arylamines or benzophenone compounds such as phenyl-α-naphthylamine, phenyl-β-naphthylamine, condensates of phenetidine and acetone, thereby obtaining more stable compositions.

When the compounds of the formula (1) of the invention are used as an insecticide, they are used in an amount of from 0.0001 to 95 wt.%, preferably from 0.01 to 50 wt.% of the insecticide.

When the insecticide of the invention is applied, the effective ingredient is used at a concentration of from 0.01 to 5000 ppm, preferably from 0.1 to 1000 ppm.

The application amount per 10 ares is generally in the range of from 1 to 300 g of the effective ingredient.

EXAMPLES

The present invention is more particularly described by way of examples, which, should not be construed as limiting the invention.

EXAMPLE 1 (COMPOUND NO. 18)

A mixture comprising 7.0 g of 1-{2-(3,4-dichlorophenyl)vinyl}-2-nitroiminoimidazolidine, 7.5 g of 2-chloro-5-chloromethylpyridine, 6.4 g of potassium carbonate and 50 ml of dimethylsulfoxide was stirred at 60° C. for one hour. The reaction mixture was poured into water, extracted with ethyl acetate, washed with water, dried (with anhydrous MgS04) and concentrated o give an oily residue. This was purified by column chromatography (silica gel, eluent: ethyl acetate) to give 5.7 g of 1-(2-chloropyridin-5-ylmethyl)-2-nitroimino-3-(3,4-dichlorphenylvinyl) -imidazolidine.

EXAMPLE 2 (COMPOUND NO. 20)

A mixture comprising 5.0 g of 1-{2-(3-cyanophenyl)vinyl}-2-nitroiminimidazolidine, 7.4 g of 2-chloro-5-chloromethylpyridine, 5.4 g of potassium carbonate and 50 ml of dimethylsulfoxide was stirred at 60° C. for one hour. The reaction mixture was poured into water, extracted with ethyl acetate, washed with water, dried (with anhydrous MgSO4) and concentrated to give an oily residue. To this was added ethyl ether, and the crystals precipitated out were filtered out and dried to give 5.9 g of 1-(2-chloropyridin-5-ylmethyl)-2-nitroimino-3-{2-(3-cyanophenyl)vinyl}-imidazolidine.

EXAMPLE 3 (COMPOUND NO. 23)

A mixture comprising 15.4 g of 1-(2,2-diphenylvinyl)-2-nitroiminoimidazolidine, 8.1 g of 2-chloro-5-chloromethylpyridine, 6.9 g of potassium carbonate and 80 ml of dimethylsulfoxide was stirred at 60° C. for 2 hours. The reaction mixture was poured into water, extracted with ethyl acetate, washed with water, dried (with anhydrous MgSO4) and concentrated to give a crude product. To this was added 100 ml of ethyl acetate for recrystallization, and 13 g of 1-(2-chloropyridin-5-ylmethyl)-2-nitroimino-3-(2,2-diphenylvinyl)imidazolidine was obtained.

EXAMPLE 4 (COMPOUND NO. 25)

A mixture comprising 5.0 g of 1-{4-(2,2,2-trifluoroethoxy)phenylvinyl}-2-nitroiminoimidazolidine, 5.8 g of 2-chloro-5-chloromethylpyridine, 8.4 g of potassium carbonate and 30 ml of dimethylsulfoxide was stirred at 60° C. for one hour. The reaction mixture was poured into water, extracted with ethyl acetate, washed with water, dried (with anhydrous MgSO4) and concentrated to give an oily residue. This was purified by column chromatography (silica gel, eluent: ethyl acetate/hexane=4/1) to give 4.9 g of 1-(2-chloropyridin-5-ylmethyl)-2-nitroimino-3-{4-(2,2,2-trifluoroethoxy)phenylvinyl}-imidazolidine.

EXAMPLE 5 (COMPOUND NO. 26)

A mixture comprising 6.0 g of 1-(1-propenyl)-2nitroiminoimidazolidine, 7.0 g of potassium carbonate, 70 ml of DMSO and 7.4 g of 2-chloro-5-chloromethylpyridine was stirred at 60° C. for one hour. The reaction mixture was poured into water, extracted with ethyl acetate, washed with water, dried (with anhydrous MgSO4) and concentrated to give an oily residue. This was purified by column chromatography (silica gel, eluent: ethyl acetate/hexane=2/1) to give 8.6 g of 1-(2-chloropyridin-5-ylmethyl)-2-nitroimino -3- (1propenyl)imidazolidine.

EXAMPLE 6 (COMPOUND NO. 33)

A mixture comprising 3.7 g of 1-(2 ethyl-1-hexenyl)-2-nitroiminoimidazolidine, 3.3 g of 2-chloro-5chloromethylpyridine, 4.4 g of potassium carbonate and 20 ml of dimethylsulfoxide was stirred at 60° C. for one hour. The reaction mixture was poured into water, extracted with ethyl acetate, washed with water, dried (with anhydrous MgSO4) and concentrated to give an oily residue. This was purified by column chromatography (silica gel, eluent: ethyl acetate/hexane 2/1) to give 4.3 g of 1-(2-chloropyridin-5-ylmethyl)-2-nitroimino-3-(2-ethyl-1hexenyl)imidazlidine.

EXAMPLE 7 (COMPOUND NO. 35, COMPOUND NO. 36)

A mixture comprising 20.0 g of 1-(2-methoxyvinyl)2-nitroiminoimidaozlidine, 18.0 g of 2-chloro-5chloromethylpyridine, 15.0 g of potassium carbonate and 150 ml of dimethylsulfoxide was stirred at 70° C. for 2 hours. The reaction mixture was poured into water, extracted with ethyl acetate, washed with water, dried (with anhydrous MgSO4) and concentrated to give an oily residue. This was purified by column chromatography (silica gel, eluent: ethyl acetate) to give 9.8 g of 1-(2 chloropyridin-5-ylmethyl)-2-nitroimino-3-(cis-2methoxyvinyl)imidazolidine and 0.58 g of 1-(2-chloropyridin-5-ylmethyl)-2-nitroimino-3-(trans-2methoxyvinyl-)imidazolidine.

EXAMPLE 8 (Compound No. 37)

A mixture comprising 2.8 g of 1-(2-phenoxyvinyl)2-nitroiminoimidazolidine, 3.6 g of 2-chloro-5chloromethylpyridine, 3.2 g of potassium carbonate and 15 ml of dimethylsulfoxide was stirred at 70° C. for one hour. The reaction mixture was poured into water, extracted with ethyl acetate, washed with water, dried (with anhydrous $MgSO_4$) and concentrated to give an oily residue. This was purified by column chromatography (silica gel, eluet: ethyl acetate) to give 3.0 g of 1-(2-chloropyridin-5-ylmethyl)-2-nitroimino-3-(2-phenoxyvinyl)-imidazolidine.

EXAMPLE 9 (COMPOUND NO. 38)

A mixture comprising 3.0 g of 1-(formylvinyl)-2-nitroiminoimidazolidine, 0.7 g of sodium hydride and 30 ml of DMF was stirred at 40° C. for 15 minutes. After this was cooled to room temperature, 3.2 g of 2-chloro-5-chloromethylpyridine was added thereto and stirred at 60° C for 2 hours. The reaction mixture was poured into water, extracted with ethyl acetate, washed with water, dried (with anhydrous $MgSO_4$) and concentrated to give an oily residue. This was purified by column chromatography (silica gel, eluent: ethyl acetate) to give 2.3 g of 1-(2-chloropyridin-5-ylmethyl)-2-nitroimino-3-(2-formylvinyl)imidazolidine.

EXAMPLE 10 (COMPOUND NO. 42)

A mixture comprising 8.0 g of 1-(2-ethylthiovinyl)-2-nitroiminoimidazolidine, 7.2 g of 2-chloro-5-chloromethylpyridine, 20.0 g of potassium carbonate .and 30 ml of dimethylsulfoxide was stirred at 60° C. for 30 minutes. The reaction mixture was poured into water, extracted with ethyl acetate, washed with water, dried (with anhydrous MgSO) and concentrated to give an oily residue. This was purified by column chromatography silica gel, eluent: ethyl acetate/hexane 4/1) to give 8.3 g of 1-(2-chloropyridin-5-ylmethyl)-2-nitroimino-3-(2-ethylthiovinyl)imidazolidine.

EXAMPLE 11 (COMPOUND NO. 43)

A mixture comprising 6.0 g of 1{2-(2-chloropyridin-5-yl)vinyl}-2-nitroiminoimidazolidine, 8.0 g of 2-chloro-5-chloromethylpyridine, 6.8 g of potassium carbonate and 60 ml of dimethylsulfoxide was stirred at 75° C. for 2.5 hours. The reaction mixture was poured into water, extracted with ethyl acetate, washed with water, dried (with anhydrous $MgSO_4$) and concentrated to give an oily residue. This was purified by column chromatography (silica gel, eluent: ethyl acetate) to give 3.9 of 1-(2 chloropyridin-5-ylmethyl)-2-nitroimino-3-{trans-2-(2-chloropyridin-5-yl)vinyl}imidazolidine.

EXAMPLE 12 (Compound No. 45)

A mixture comprising 6.9 g of 1-(2-phenylvinyl)-2-nitroiminoimidaozlidine, 10.0 g of 2-chloro-5-chloromethylthiazole, 8.2 g of potassium carbonate and 30 ml of dimethylsulfoxide was stirred at 60° C. for one hour. The reaction mixture was poured into water, extracted with ethyl acetate, washed with water, dried (with anhydrous $MgSO_4$) and concentrated to give an oily residue. This was purified by column chromatography (silica gel, eluent: ethyl acetate) to give 7.9 g of 1-(2-chlorothiazol-5-ylmehtyl)-2-nitroimino-3-(2-phenylvinyl)-imidazolidine.

In the same manner as in the preceding Examples 1 to 12, other compounds of the formula (1) were prepared, which were shown in Table 1 and Table 2 below along with the compounds prepared in the preceding examples.

TABLE 1

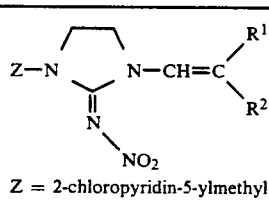

(1)

Z = 2-chloropyridin-5-ylmethyl

| Compound No. | $R^1$ | $R^2$ | Value of Physical Properties |
|---|---|---|---|
| 1 | H | H | $\delta_{TMS}$ (CDCL$_3$) (ppm): 3.67~3.72(2H, m), 3.87~3.92(2H, m), 4.48(1H, d, J=15.4Hz), 4.55(2H, s), 4.62(1H, d, J=8.8Hz), 6.73(1H, dd, J=15.4Hz, J=8.8Hz), 7.38(1H, d, J=8.1Hz), 7.73(1H, dd, J=8.1Hz, J=2.2Hz), 8.34(1H, d, J=2.2Hz) $\nu_{MAX}$ (KBr) (cm$^{-1}$): 1636, 1559, 1460, 1260, 1107, 849, 749 m.p.: 79.5~83.9° C. |
| 2 | H | Ph | $\delta_{TMS}$ (CDCl$_3$) (ppm): 3.75~3.80(2H, m), 4.00~4.08(2H, m), 4.58(2H, s), 5.96(1H, d, J=14.6Hz), 7.17~7.40(7H, m), 7.77(1H, d, d, J=8.8Hz, J=2.2Hz), 8.38(1H, d, J=2.2Hz) $\nu_{MAX}$ (KBr) (cm$^{-1}$): 1655, 1558, 1527, 1481, 1391, 1250, 1096, 946, 752, 696 m.p.: 180-183° C. (dec.) |
| 3 | H | 2-CH$_3$—Ph | $\delta_{TMS}$ (CDCl$_3$) (ppm): 2.30(3H, s), 3.69~3.73(2H, m), 4.02~4.06(2H, m), 4.56 (2H, s), 6.06(1H, d, J=14.7Hz), 7.07(1H, d, J=13.9Hz), 7.13~7.17(3H, m), 7.34~7.39 (2H, m), 7.74~7.77(1H, m), 8.35(1H, s) $\nu_{MAX}$ (KBr) (cm$^{-1}$): 1641, 1548, 1513, 1460, 1416, 1394, 1340, 1265, 1103, 938, 828, 772 m.p.: 159.2~161.2° C. |
| 4 | H | 3-CH$_3$—Ph | $\delta_{TMS}$ (CDCl$_3$): 2.33(3H, s), 3.68~3.72(2H, m), 3.98~4.02(2H, m), 4.54(2H, s), 5.88(1H, d, J=14.7Hz), 7.03~7.23(5H, m), 7.37(1H, d, J=8.8Hz), 7.75(1H, dd, J=8.1Hz, J=2.9Hz), 8.34(1H, d, J=2.2Hz) $\nu_{MAX}$ (KBr) (cm$^{-1}$): 1650, 1562, 1518, 1417, 1267, 1108, 1025, 950, 817, 779, 697 m.p. 175.6~176.3° C. |
| 5 | H | 4-CH$_3$—Ph | $\delta_{TMS}$ (CDCl$_3$) (ppm): 2.33(3H, s), 3.66~3.71(2H, m), 3.98~4.02(2H, m), 4.55 (2H, s), 5.89(1H, d, J=14.7Hz), 7.11(2H, d, J=8.1Hz), 7.18(1H, d, J=14.7Hz), 7.20 (2H, d, J=8.1Hz), 7.38(1H, d, J=8.1Hz), 7.76(1H, d, J=8.1Hz), 8.34(1H, s) $\nu_{MAX}$ (KBr) (cm$^{-1}$): 3448, 1649, 1559, 1524, 1509, 1478, 1460, 1388, 1339, 1257, |

TABLE 1-continued

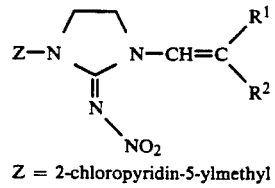

Z = 2-chloropyridin-5-ylmethyl

| Compound No. | R¹ | R² | Value of Physical Properties |
|---|---|---|---|
| | | | 1102, 951, 848, 808, 749 |
| | | | m.p.: 168.5~169.1° C. |
| 6 | H | 4-tert-Bu—Ph | $\delta_{TMS}$ (CDCl$_3$) (ppm): 1.31(9CH, s), 3.69~3.71(2H, m), 3.98~4.01(2H, m), 4.54 (2H, s), 5.91(1H, d, J=14.7Hz), 7.18(1H, d, J=14.7Hz), 7.23~7.34(4H, m), 7.37 (2H, d, J=8.1Hz), 7.73~7.76(1H, m), 8.34(1H, d, J=2.2Hz) |
| | | | $\nu_{MAX}$(KBr) (cm$^{-1}$): 1647, 1559, 1512, 1462, 1428, 1389, 1256, 1109, 1024, 960, 847 |
| | | | m.p.: 170.1~171.6° C. |
| 7 | H | 2,4-(CH$_3$)$_2$Ph | $\delta_{TMS}$ (CDCl$_3$) (ppm): 2.27(3H, s), 2.30(3H, s), 3.67~3.72(2H, m), 4.01~4.05 (2H, m), 4.56(2H, s), 6.04(1H, d, J=13.9Hz), 6.97(2H, d, J=8.8Hz), 7.04(1H, d, J=14.7Hz), 7.24(1H, s), 7.38(1H, d, J=8.1Hz), 7.76(1H, d, J=8.8Hz), 8.35(1H, s) |
| | | | $\nu_{MAX}$(KBr) (cm$^{-1}$): 1648, 1564, 1515, 1466, 1426, 1389, 1330, 1287, 1260, 1100, 1030, 932, 830 |
| | | | m.p.: 162.0~163.3° C. |
| 8 | H | 2,5-(CH$_3$)$_2$Ph | $\delta_{TMS}$ (CDCl$_3$) (ppm): 2.26(3H, s), 2.31(3H, s), 3.68~3.73(2H, m), 4.01~4.05 (2H, m), 4.56(2H, s), 6.04(1H, d, J=14.7Hz), 6.96(1H, d, J=8.1Hz), 7.02(1H, d, J=8.1Hz), 7.09(1H, d, J=14.7Hz), 7.17(1H, s), 7.38(1H, d, J=8.1Hz), 7.76(1H, d, J=8.1Hz), 8.35(1H, s) |
| | | | $\nu_{MAX}$(KBr) (cm$^{-1}$): 1644, 1574, 1556, 1519, 1455, 1426, 1265, 1141, 1103, 1029, 943 |
| | | | m.p.: 152.1~153.2° C. |
| 9 | H | 3,4-(CH$_3$)$_2$Ph | $\delta_{TMS}$ (CDCl$_3$) (ppm): 2.24(6H, s), 3.67~3.71(2H, m), 3.97~4.02(2H, m), 4.53 (2H, s), 5.87(1H, d, J=14.8Hz), 7.01~7.19(4H, m), 7.36(1H, d, J=8.8Hz), 7.74(1H, d, d, J=8.8Hz, J=2.2Hz), 8.34(1H, d, J=2.2Hz) |
| | | | $\nu_{MAX}$(KBr) (cm$^{-1}$): 1584, 1566, 1528, 1412, 1286, 1108, 961, 818 |
| | | | m.p.: 165~169° C. (dec.) |
| 10 | H | 4-CH$_3$O—Ph | $\delta_{TMS}$ (CDCl$_3$+DMSO-d$_6$) (ppm): 3.76~3.81(2H, m), 3.79(3H, s), 4.03~4.08 (2H, m), 4.59(2H, s), 5.91(1H, d, J=14.7Hz), 6.83(2H, d, J$_{AB}$=8.8Hz), 7.03(1H, J=14.7Hz), 7.24(2H, d, J$_{AB}$=8.8Hz), 7.39(1H, d, J=8.1Hz), 7.77(1H, d, d, J=8.1Hz, J=2.2Hz), 8.39(1H, d, J=2.2Hz) |
| | | | $\nu_{MAX}$(KBr) (cm$^{-1}$): 1649, 1549, 1505, 1458, 1332, 1271, 1096, 1031, 952, 845 |
| | | | m.p.: 160.5~161.5° C. (dec.) |
| 11 | H | 3,4-OCH$_2$O—Ph | $\delta_{TMS}$ (CDCl$_3$) (ppm): 3.67~3.72(2H, m), 3.97~4.02(2H, m), 4.55(2H, s), 5.85 (1H, d, J=14.7Hz), 5.96(2H, s), 6.74(2H, s), 6.82(1H, s), 7.05(1H, d, J=14.7Hz), 7.38(1H, d, J=8.1Hz), 7.75(1H, d, J=8.1Hz), 8.35(1H, s) |
| | | | $\nu_{MAX}$(KBr) (cm$^{-1}$): 1711, 1653, 1558, 1525, 1465, 1445, 1390, 1257, 1104, 1038, 945, 930, 832, 803 |
| | | | m.p.: 119.1~121.6° C. |
| 12 | H | 2-Cl—Ph | $\delta_{TMS}$ (CDCl$_3$) (ppm): 3.81~3.86(2H, m), 4.08~4.13(2H, m), 4.61(2H, s), 6.26 (1H, d, J=14.7Hz), 7.15~7.47(6H, m), 7.78(1H, d, d, J=8.1Hz, J=2.2Hz), 8.40(1H, d, J=2.2Hz) |
| | | | $\nu_{MAX}$(KBr) (cm$^{-1}$): 1646, 1567, 1511, 1463, 1414, 1261, 1109, 933, 821, 761 |
| | | | m.p.: 189~190° C. (dec.) |
| 13 | H | 3-Cl—Ph | $\delta_{TMS}$ (CDCl$_3$) (ppm): 3.97~4.02(2H, m), 4.13~4.18(2H, m), 4.66(2H, s), 6.09 (1H, d, J=14.6Hz), 7.29~7.43(5H, m), 7.48(1H, d, J=8.1Hz), 7.90(1H, d, d, J=8.1Hz, J=2.2Hz), 8.46(1H, d, J=2.2Hz) |
| | | | $\nu_{MAX}$(KBr) (cm$^{-1}$): 1645, 1560, 1526, 1430, 1387, 1266, 1255, 1103, 956, 739 |
| | | | m.p.: 159~160.5° C. |
| 14 | H | 4-Cl—Ph | $\delta_{TMS}$ (CDCl$_3$+DMSO-d$_6$) (ppm): 3.84~3.87(2H, m), 4.04~4.06(2H, m), 4.60(2H, s), 6.02(1H, d, J=14.7Hz), 7.15(1H, J=14.7Hz), 7.28(2H, d, J$_{AB}$=8.8Hz), 7.32 (2H, d, J$_{AB}$=8.8Hz), 7.42(1H, d, J=8.1Hz), 7.82(1H, d, d, J=8.1Hz, J=2.2Hz), 8.40 (1H, d, J=2.2Hz) |
| | | | $\nu_{MAX}$(KBr) (cm$^{-1}$): 1647, 1553, 1507, 1456, 1333, 1269, 1092, 953, 812 |
| | | | m.p.: 176~177° C. (dec.) |
| 15 | H | 4-F—Ph | $\delta_{TMS}$ (DMSO-d$_6$) (ppm): 3.82~3.84(2H, m), 4.00~4.03(2H, m), 4.57(2H, s), 6.12(1H, d, J=14.7Hz), 7.03(1H, d, J=13.9Hz), 7.13(2H, t, J=8.8Hz), 7.40~7.44 (2H, m), 7.54(1H, d, J=8.1Hz), 7.84(1H, dd, J=8.8Hz, J=2.9Hz), 8.40(1H, d, J=2.9Hz) |
| | | | $\nu_{MAX}$(KBr) (cm$^{-1}$): 1651, 1553, 1505, 1466, 1260, 1099, 938, 850, 772 |
| | | | m.p. 191.4~191.7° C. |
| 16 | H | 2,3-Cl$_2$—Ph | $\delta_{TMS}$ (DMSO-d$_6$) (ppm): 3.84~3.88(2H, m), 4.06~4.11(2H, m), 4.60(2H, s), 6.23(1H, d, J=14.7Hz), 7.19(1H, d, J=14.7Hz), 7.32(1H, t, J=8.1Hz), 7.47~7.49 (1H, m), 7.54~7.59(1H, m), 7.86(1H, dd, J=8.1Hz, J=2.2Hz), 8.41(1H, d, J=2.2Hz) |
| | | | $\nu_{MAX}$(KBr) (cm$^{-1}$): 1640, 1568, 1455, 1257, 1106, 823 |
| | | | m.p.: 201.0~201.5° C. |
| 17 | H | 2,4-Cl$_2$—Ph | $\delta_{TMS}$ (DMSO-d$_6$) (ppm): 3.82~3.87(2H, m), 4.04~4.09(2H, m), 4.59(2H, s), 6.13(1H, d, J=14.7Hz), 7.20(1H, d, J=14.7Hz), 7.36(1H, dd, J=8.8Hz, J=2.2Hz), 7.55 (1H, d, J=8.1Hz), 7.58(1H, d, J=2.2Hz), 7.64(1H, d, J=8.8Hz), 7.85(1H, dd, J=8.8Hz, J=2.2Hz), 8.40(1H, d, J=2.2Hz). |
| | | | $\nu_{MAX}$(KBr) (cm$^{-1}$): 1639, 1565, 1508, 1459, 1270, 1100, 936, 830 769, 752 |
| | | | m.p.: 146.7~149.2° C. |
| 18 | H | 3,4-Cl$_2$—Ph | $\delta_{TMS}$ (DMSO-d$_6$) (ppm): 3.81~3.86(2H, m), 3.99~4.03(2H, m), 4.58(2H, s), 6.09(1H, d, J=14.7Hz), 7.25(1H, d, J=14.7Hz), 7.39(1H, dd, J=8.8Hz, J=2.2Hz), 7.52 |

TABLE 1-continued

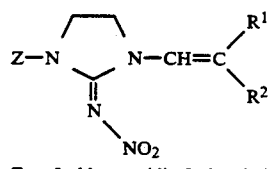

Z = 2-chloropyridin-5-ylmethyl

| Compound No. | R¹ | R² | Value of Physical Properties |
|---|---|---|---|
| | | | (1H, d, J=8.1Hz), 7.55(1H, d, J=7.3Hz), 7.69(1H, d, J=2.2Hz), 7.84(1H, dd, J=8.1Hz, J=2.2Hz), 8.40(1H, d, J=2.2Hz)<br>$\nu_{MAX}$(KBr) (cm$^{-1}$): 1648, 1562, 1511, 1437, 1273, 1133, 1107, 1026, 948, 814, 745<br>m.p.: 143.0~147.2° C. |
| 19 | H | 2,6-Cl₂—Ph | $\delta_{TMS}$ (DMSO-d₆) (ppm): 3.85~3.90(2H, m), 4.05~4.10(2H, m), 4.59(2H, s), 5.96(1H, d, J=14.7Hz), 7.24(1H, d, J=14.7Hz), 7.26(1H, t, J=8.1Hz), 7.49(2H, d, J=8.1Hz), 7.55(1H, d, J=8.1Hz), 7.86(1H, dd, J=8.1Hz, J=2.2Hz), 8.42(1H, d, J=2.2Hz)<br>$\nu_{MAX}$(KBr) (cm$^{-1}$): 1652, 1564, 1509, 1430, 1263, 1103, 944, 770<br>m.p.: 172.8~173.8° C. |
| 20 | H | 3-CN—Ph | $\delta_{TMS}$ (DMSO-d₆) (ppm): 3.83~3.87(2H, m), 4.01~4.06(2H, m), 4.59(2H, s), 6.14(1H, d, J=14.7Hz), 7.33(1H, d, J=14.7Hz), 7.48~7.56(2H, m), 7.61(1H, d, J=8.1Hz), 7.72(1H, d, J=8.1Hz), 7.85(1H, dd, J=8.1Hz, J=2.2Hz), 7.92(1H, s), 8.41(1H, d, J=2.2Hz)<br>$\nu_{MAX}$(KBr) (cm$^{-1}$): 2229, 1650, 1568, 1449, 1259, 1106, 942, 826<br>m.p.: 180.8~181.0° C. |
| 21 | H | 4-Ph—Ph | $\delta_{TMS}$ (CDCl₃) (ppm): 3.69~3.74(2H, m), 4.01~4.05(2H, m), 4.56(2H, s), 5.95(1H, d, J=14.7Hz), 7.33~7.46(7H, m), 7.54~7.61(4H, m), 7.76(1H, dd, J=8.1Hz, J=2.2Hz), 8.36(1H, d, J=2.93Hz)<br>$\nu_{MAX}$(KBr) (cm$^{-1}$): 1647, 1559, 1509, 1459, 1388, 1259, 1140, 1102, 943, 849, 763, 749, 689<br>m.p. 133.0~136.0° C. |
| 22 | H | 4-PhCO—Ph | $\delta_{TMS}$ (CDCl₃) (ppm): 3.72~3.76(2H, m), 4.00~4.05(2H, m), 4.57(2H, s), 5.93(1H, d, J=14.7Hz), 7.35~7.79(10H, m), 8.36(1H, s)<br>$\nu_{MAX}$(KBr) (cm$^{-1}$): 1649, 1599, 1561, 1514, 1459, 1390, 1259, 1189, 1178, 1149, 1103, 1027, 938, 925, 862<br>m.p.: 149.0~149.3° C. |
| 23 | Ph | Ph | $\delta_{TMS}$ (CDCl₃) (ppm): 3.27~3.39(4H, m), 4.53(1H, s), 6.56(1H, s), 7.13~7.15 (2H, m), 7.26~7.28(4H, m), 7.33~7.40(5H, m), 7.70(1H, dd, J=2.9Hz, J=7.1Hz), 8.29(1H, d, J=1.5Hz)<br>$\nu_{MAX}$(KBr) (cm$^{-1}$): 1737, 1555, 1511, 1466, 1390, 1259, 1140, 1106, 1035, 766, 699<br>m.p.: 179~181° C. |
| 24 | H | 4-CF₃—Ph | $\delta_{TMS}$ (CDCl₃) (ppm): 3.70~3.74(2H, m), 3.98~4.03(2H, m), 4.57(2H, s), 5.89 (1H, d, J=14.7Hz), 7.16(1H, d, J=8.1Hz), 7.21(1H, d, J=13.9Hz), 7.32(1H, d, J=8.8Hz), 7.39(1H, d, J=8.1Hz), 7.75(1H, d, J=8.8Hz), 8.36(1H, s)<br>$\nu_{MAX}$(KBr) (cm$^{-1}$): 1650, 1587, 1566, 1507, 1459, 1413, 1380, 1287, 1214, 1158, 1110, 1029, 964, 869<br>m.p.: 170.5~171.7° C. |
| 25 | H | 4-CF₃CH₂O—Ph | $\delta_{TMS}$ (DMSO-d₆) (ppm): 3.80~3.84(2H, m), 4.01~4.06(2H, m), 4.58(2H, s), 4.73(2H, q, J=8.8Hz), 6.10(1H, d, J=14.7Hz), 7.01(1H, d, J=14.7Hz), 7.01(2H, d, J=8.8Hz), 7.35(2H, d, J=8.8Hz), 7.55(1H, d, J=2.1Hz), 7.84(1H, dd, J=8.1Hz, J=2.2Hz), 8.40(1H, d, J=1.9Hz)<br>IR cm$^{-1}$ (KBr): 1649, 1587, 1510, 1459, 1412, 1378, 1287, 1166, 1108, 1080, 976, 826, 665<br>m.p. 162.8~165.2° C. |
| 26 | H | CH₃ | $\delta_{TMS}$ (CDCl₃) (ppm): 1.74(1H, dd, J=1.5Hz, J=6.6Hz), 3.64~3.69(2H, m), 3.86~3.91(2H, m), 5.04(1H, qd, J=6.6Hz, J=13.9Hz), 6.46(1H, dd, J=1.5Hz, J=13.9Hz), 7.36(1H, d, J=8.1Hz), 7.72(1H, dd, J=2.2Hz, J=8.1Hz), 8.33(1H, d, J=2.2Hz)<br>$\nu_{MAX}$(neat) (cm$^{-1}$): 2921, 1558, 1524, 1461, 1388, 1260, 1103, 940<br>m.p.: 94.4~94.7° C. |
| 27 | H | CH(CH₃)₂ | $\delta_{TMS}$ (CDCl₃) (ppm): 0.99(6H, d, J=6.6Hz), 2.18~2.24(1H, m), 3.51~3.56 (2H, m), 3.80~3.89(2H, m), 4.55(2H, s), 4.99(1H, dd, J=14.7Hz, J=6.6Hz), 6.46(1H, d, J=14.7Hz), 7.35(1H, d, J=8.1Hz), 7.71(1H, dd, J=8.1Hz, J=2.9Hz), 8.32(1H, d, J=2.9Hz)<br>$\nu_{MAX}$(KBr) (cm$^{-1}$): 2960, 1558, 1522, 1457, 1388, 1258, 1106<br>m.p.: 130~136° C. (dec.) |
| 28 | H | n-C₄H₉ | $\delta_{TMS}$ (CDCl₃) (ppm): 0.89(3H, t, J=6.6Hz), 1.24~1.39(4H, m), 2.05~2.10 (2H, m), 3.64~3.68(2H, m), 3.86~3.91(2H, m), 4.53(2H, s), 5.03(1H, d, t, J=13.9Hz, J=7.3Hz), 6.68(1H, d, J=13.9Hz), 7.36(1H, d, J=8.8), 7.73(1H, d, d, J=8.8Hz, J=2.2Hz), 8.33(1H, d, J=2.2Hz)<br>$\nu_{MAX}$(KBr) (cm$^{-1}$): 1664, 1560, 1431, 1251, 1100, 950, 859, 759, 735<br>m.p.: 107~117° C. |
| 29 | H | n-C₆H₁₃ | $\delta_{TMS}$ (CDCl₃) (ppm): 0.88(3H, t, J=6.6Hz), 1.26~1.37(8H, m), 2.04~2.09(2H, m), 3.63~3.68(2H, m), 3.86~3.90(2H, m), 4.53(2H, s), 5.02(1H, d, t, J=13.9Hz, J=7.3Hz), 6.47(1H, d, J=13.9Hz), 7.36(1H, d, J=8.1), 7.73(1H, d, d, J=8.1Hz, J=2.2Hz), 8.33(1H, d, J=2.2Hz)<br>$\nu_{MAX}$(neat) (cm$^{-1}$): 1664, 1558, 1522, 1462, 1389, 1259, 1105, 941, 818, 749<br>$n_D$(25° C.): 1.5713 |
| 30 | H | n-C₈H₁₇ | $\delta_{TMS}$ (CDCl₃) (ppm): 0.88(3H, t, J=6.6Hz), 1.23~1.38(12H, m), 2.06(2H, dt, J=6.6Hz, J=6.6Hz), 3.60~3.65(2H, m), 3.81~3.89(2H, m), 4.52(2H, S), 5.01(1H, dt, J=13.9Hz, J=7.3Hz), 6.48(1H, d, J=13.9), 7.36(1H, d, J=8.1Hz), 7.73(1H, dd, |

TABLE 1-continued

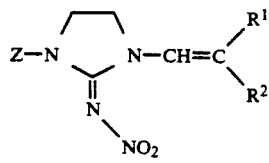

(1)

Z = 2-chloropyridin-5-ylmethyl

| Compound No. | R¹ | R² | Value of Physical Properties |
|---|---|---|---|
| | | | J=2.2Hz, J=8.1Hz), 8.32(1H, d, J=2.2Hz)<br>$\nu_{MAX}$ (neat) (cm⁻¹): 2926, 2855, 1559, 1523, 1460, 1389, 1259, 1104, 942 |
| 31 | H | n-C₁₀H₂₁ | $n_D$ (17° C.): 1.5546<br>$\delta_{TMS}$(CDCl₃) (ppm): 0.88(3H, t, J=6.6Hz), 1.26~1.41(20H, m), 2.04~2.09(2H, m), 3.60~3.65(2H, m), 3.84~3.88(2H, m), 4.52(2H, S), 5.00(1H, dt, J=7.3Hz, J=14.7Hz), 6.48(1H, d, J=14.7Hz), 7.36(1H, d, J=8.1Hz), 7.73(1H, dd, J=8.1Hz, J=2.2Hz), 8.32(1H, d, J=2.2Hz)<br>$\nu_{MAX}$ (neat) (cm⁻¹): 2925, 2854, 1558, 1523, 1462, 1390, 1259, 1104 |
| 32 | CH₃ | CH₃ | $\delta_{TMS}$(CDCl₃) (ppm): 1.72(6H, d, J=1.5Hz), 3.59~3.63(2H, m), 3.82~3.87 (2H, m), 4.53(2H, s), 5.71(1H, broad-s), 7.36(1H, d, J=8.8), 7.72(1H, d, d, J=8.8Hz, J=2.2Hz), 8.31(1H, d, J=2.2Hz)<br>$\nu_{MAX}$ (neat) (cm⁻¹): 1557, 1456, 1388, 1260, 1141, 1107, 1027, 817, 749 |
| 33 | C₂H₅ | n-C₄H₉ | $n_D$ (25° C.): 1.5696<br>$\delta_{TMS}$(CDCl₃) (ppm): 0.88~0.92(3H, m), 1.00~1.06(3H, m), 1.24~1.52(4H, m), 1.97~2.14(4H, m), 3.53(2H, t, J=9.5Hz), 3.78(2H, t, J=9.5Hz), 4.51(2H, s), 5.71(1H, s), 7.36(1H, J=8.8Hz), 7.71~7.74(1H, m), 8.31(1H, d, J=2.2Hz)<br>$\nu_{MAX}$ (neat) (cm⁻¹): 2961, 2933, 2873, 1550, 1460, 1388, 1260, 1107 |
| 34 | CH₃ | Ph | $\delta_{TMS}$(CDCl₃) (ppm): 2.11(3H, d, J=2.5Hz), 3.57~3.62(2H, m), 3.92~3.96(2H, m), 4.55(2H, s), 6.19(1H, d, J=2.5Hz), 7.29~7.39(6H, m), 7.75(1H, d, d, J=8.8Hz, J=2.9Hz), 8.34(1H, d, J=2.9Hz)<br>$\nu_{MAX}$ (KBr) (cm⁻¹): 1552, 1509, 1445, 1378, 1311, 1282, 1101, 1021, 764, 701<br>m.p.: 137~139° C. (dec.) |
| 35 | H | OCH₃-cis | $\delta_{TMS}$(CDCl₃) (ppm): 3.57~3.59(2H, m), 3.67(3H, s), 4.08~4.13(2H, m), 4.51 (2H, s), 5.31(1H, d, J=5.1Hz), 5.72(1H, d, J=5.1Hz), 7.36(1H, d, J=8.1Hz), 7.71(1H, d, d, J=8.1Hz, J=2.9Hz), 8.32(1H, d, J=2.9Hz)<br>$\nu_{MAX}$ (neat) (cm⁻¹): 1558, 1521, 1462, 1393, 1258, 1101, 969, 945, 817, 748<br>m.p.: 117.0~118.8° C |
| 36 | H | OCH₃-trans | $\delta_{TMS}$(CDCl₃) (ppm): 3.57(3H, s), 3.61~3.66(2H, m), 3.80~3.85(2H, m), 4.51 (2H, s), 6.08(1H, d, J=11.7Hz), 6.46(1H, d, J=11.7Hz), 7.36(1H, d, J=8.1Hz), 7.72 (1H, d, d, J=8.1Hz, J=2.9Hz), 8.32(1H, d, J=2.9Hz)<br>$\nu_{MAX}$ (neat) (cm⁻¹): 1558, 1463, 1388, 1264, 1134, 1105, 1028, 983, 819, 749<br>m.p.: 89.2~90.0° C. |
| 37 | H | OPh | $\delta_{TMS}$(DMSO-d₆) (ppm): 3.76~3.81(2H, m), 3.96~4.00(2H, m), 4.55(2H, s), 6.51(1H, d, J=11.0Hz), 6.91(1H, d, J=11.0Hz), 7.09~7.11(3H, m), 7.35~7.39 (2H, m), 7.55(1H, d, J=8.1Hz), 7.82(1H, dd, J=8.1Hz, J=2.2Hz), 8.39(1H, d, J=2.2Hz)<br>$\nu_{MAX}$ (KBr) (cm⁻¹): 1586, 1413, 1383, 1288, 1230, 1115, 756, 693 |
| 38 | H | CHO | $\delta_{TMS}$(CDCl₃) (ppm): 3.77~3.81(2H, m), 3.89~3.94(2H, m), 7.26(2H, s), 5.56(1H, dd, J=7.3Hz, J=13.9Hz), 7.40(1H, d, J=8.1Hz), 7.62~7.74(2H, m), 8.37(1H, d, J=2.9Hz), 9.46(1H, d, J=8.1Hz)<br>$\nu_{MAX}$ (neat) (cm⁻¹): 1672, 1625, 1586, 1494, 1390, 1263, 1125, 955, 821, 749 |
| 39 | H | n-C₄F₉ | $n_D$ (26° C.): 1.5625<br>$\delta_{TMS}$(CDCl₃) (ppm): 3.73~3.77(2H, m), 3.84~3.89(2H, m), 4.54(2H, s), 4.92 (1H, q, J=13.9Hz), 7.32~7.42(2H, m), 7.73(1H, dd, J=2.2Hz, J=8.1Hz), 8.35(1H, d, J=2.2Hz)<br>$\nu_{MAX}$ (neat) (cm⁻¹): 2928, 1669, 1586, 1508, 1460, 1352, 1236, 1133, 888, 745 |
| 40 | H | CH₂Ph | $n_D$ (16° C.): 1.4849<br>$\delta_{TMS}$(CDCl₃) (ppm): 3.39(2H, d, J=7.3Hz), 3.61~3.66(2H, m), 3.84~3.88(2H, m), 4.53(2H, s), 5.12~5.16(1H, m), 6.62(1H, d, J=13.9Hz), 7.16~7.31(5H, m), 7.36(1H, d, J=8.1Hz), 7.73(1H, dd, J=8.1Hz, J=2.2Hz), 8.32(1H, d, J=2.2Hz)<br>$\nu_{MAX}$ (neat) (cm⁻¹): 1711, 1664, 1557, 1520, 1461, 1390, 1258, 1140, 1104, 1028, 943 |
| 41 | H | NHCOPh | $\delta_{TMS}$(DMSO-d₆) (ppm): 3.73~3.77(2H, m), 3.99~4.03(2H, m), 4.58(2H, s), 6.86~6.95(2H, m), 7.37~7.57(4H, m), 7.75(1H, dd, J=8.1Hz, J=2.2Hz), 7.95(2H, d, J=7.3Hz), 8.37(1H, d, J=2.2Hz)<br>$\nu_{MAX}$ (KBr) (cm⁻¹): 3341, 1676, 1530, 1406, 1135, 1100, 918<br>m.p.: 220~221° C. (dec.) |
| 42 | H | SC₂H₅ | $\delta_{TMS}$(CDCl₃) (ppm): 1.29(3H, t, J=7.3Hz), 2.66(2H, q, J=7.3Hz), 3.60~3.67 (2H, m), 3.87~4.12(2H, m), 4.53(2H, s), 5.55(1H, d, J=13.9Hz), 6.80(1H, d, J=13.9Hz), 7.80(1H, d, J=8.1Hz), 7.33(1H, dd, J=2.2Hz, J=8.1Hz), 8.33(1H, d, J=2.2Hz)<br>$\nu_{MAX}$ (KBr) (cm⁻¹): 1561, 1510, 1439, 1292, 1267, 1103, 838<br>m.p.: 135.0~136.0° C. |
| 43 | H | 2-Cl-pyridin-5-yl | $\delta_{TMS}$(CDCl₃) (ppm): 3.83~3.87(2H, m), 4.01~4.06(2H, m), 4.58(2H, s), 6.20 (1H, d, J=14.7Hz), 7.34(1H, d, J=14.7Hz), 7.42(1H, d, J=8.1Hz), 7.55(1H, d, J=8.1Hz), 7.84(1H, dd, J=8.1Hz, J=2.8Hz), 7.95(1H, dd, J=8.1Hz, J=2.9Hz), 8.40(2H, s)<br>$\nu_{MAX}$ (KBr) (cm⁻¹): 1648, 1579, 1558, 1501, 1456, 1269, 1101, 952<br>m.p.: 186° C. (dec.) |
| 44 | H | 4-CH₃S—Ph | $\delta_{TMS}$(CDCl₃) (ppm): 2.48(3H, s), 3.68~3.72(2H, m), 3.98~4.02(2H, m), 4.55 (2H, s), 5.87(1H, d, J=14.7Hz), 7.18(2H, d, J=8.1Hz), 7.19(2H, d, J=14.7Hz), 7.23(2H, d, J=8.1Hz), 7.38(1H, d, J=2.2Hz), 7.75(1H, dd, J=2.2Hz, J=8.1Hz), 8.35(1H. d, J=2.2Hz)<br>$\nu_{MAX}$ (KBr) (cm⁻¹): 1649, 1561, 1514, 1460, 1388, 1260, 1098, 949 |

TABLE 1-continued

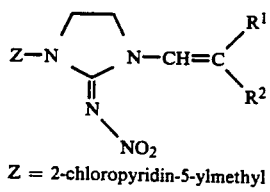

Z = 2-chloropyridin-5-ylmethyl

| Compound No. | R¹ | R² | Value of Physical Properties |
|---|---|---|---|
| | | | m.p.: 173.2~174.0° C. |

TABLE 2

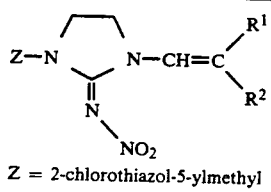

Z = 2-chlorothiazol-5-ylmethyl

| Compound No. | R¹ | R² | Value of Physical Properties |
|---|---|---|---|
| 45 | H | Ph | $\delta_{TMS}$(DMSO-d$_6$)(ppm):3.79~3.84 (2H, m), 4.00~4.04(2H, m), 4.70(2H, s), 6.12(1H, d, J=14.7Hz), 7.07(1H, d, J=14.7Hz), 7.20(1H, t, J=7.3Hz), 7.31(2H, t, J=7.3Hz), 7.37(2H, d, J=7.3Hz), 7.72(1H, s). $\nu_{MAX}$(KBr)(cm$^{-1}$):1650, 1561, 1517, 1448, 1257, 1046, 945, 752 m.p.:110° C.<(dec.) |
| 46 | CH$_3$ | CH$_3$ | $\delta_{TMS}$(CDCl$_3$)(ppm):1.71(6H, d, J=14.7Hz), 3.57~3.61(2H, m), 3.76~3.80 (2H, m), 4.61(2H, s), 5.69(1H, s), 7.47 (1H, s) $\nu_{MAX}$(neat)(cm$^{-1}$):2916, 1526, 1453, 1259, 1047 |

Next, preparation of intermediates of the formula (2) is mentioned below by way of the following examples.
Example 13 (Intermediate No. 1):

A mixture comprising 6.0 g of 2-nitroimidazolidine, 1.22 g of phenylacetaldehyde (50 % in diethyl phthalate), 60 ml of dimethylformamide and 0.05 g of boron trifluoride ether complex was stirred at 80° C. for one hour. The reaction mixture was poured into water, extracted with ethyl acetate, washed with water, dried (with anhydrous MgSO$_4$) and concentrated. The crystals thus precipitated out were sludged with ether and dried to give 4.3 g of 1 -(2-phenylvinyl) - 2-nitroiminoimidazolidine.

EXAMPLE 14 (INTERMEDIATE NO. 9)

2.59 g of methyl methylsulfinyl methylsulfide and 4.26 g of trifluorobenzyl chloride were dissolved in 30 ml of THF in nitrogen atmosphere, and 29 ml of n-butyl lithium (1.6 M hexane solution) was dropwise added thereto at −70° C. After addition, this was stirred for 40 minutes at −70° C. and then for 3 hours at room temperature. Water was added to the reaction mixture, which was then extracted with ethyl acetate, washed with water and dried (with anhydrous MgSO$_4$). After the solvent was removed by distillation, a black oil was obtained. To this were added 1.52 g of nitroiminoimidazolidine and 20 ml of DMF. Then, one ml of concentrated hydrochloric acid was added thereto at 80° C. and stirred for 4 hours at the same temperature. Water was added to the reaction mixture, which was then extracted with ethyl acetate, washed with water and dried (with anhydrous MgSO). After the solvent was removed by distillation, a solid was obtained, which was then sludged with ether to give 0.87 g of yellow crystals of 1-{4-(2,2,2-trifluoroethoxy)phenylvinyl}-2-nitroiminoimidazolidine.

EXAMPLE 15 (INTERMEDIATE NO. 20)

A mixture comprising 5.0 g of 3,4-dichlorobenzyl chloride, 0.68 g of magnesium turning and 30 ml of ethyl ether was ultrasonically treated at room temperature to prepare a Grignard reagent. After the magnesium turning was lost, 4.2 g of ethyl orthoformate and 30 ml of toluene were added, and ethyl ether was removed by distillation. Afterwards, the reaction mixture was heated under reflux for 1.5 hours. This was poured into water, extracted with ethyl acetate, washed with water, dried (with anhydrous MgSO$_4$) and concentrated to give 6.5 g of an oily residue, to which were added 2.5 g of nitroiminoimidazolidine and 25 ml of 1,3-dimethyl-2-imidazolidinone. To the resulting mixture was added 0.07 g of boron trifluoride ether complex at 90° C., and this was stirred for 1.5 hours at the same temperature. The reaction mixture was poured into water, extracted with ethyl acetate, washed with water, dried (with anhydrous MgSO$_4$) and concentrated to give an oily residue. Ether was added to the residue, and the crystals thus precipitated out were filtrated and dried to give 2.3 g of 1-(3,4-dichlorophenylvinyl)-2-nitroiminoimidazolidine.

EXAMPLE 16 (Intermediate No. 21)

3.48 g of methyl methylsulfinyl methylsulfide was dissolved in 30 ml of THF in nitrogen atmosphere, and 18 ml of n-butyl lithium (1.6 M hexane solution) was dropwise added thereto at −78° C. and stirred for 10 minutes at the same temperature. A solution of 5.0 g of m-bromomethylbenzonitrile as dissolved in 20 ml of THF was dropwise added thereto and then stirred for 2 hours at the same temperature. Water was added to the reaction mixture, which was then extracted with ethyl acetate, washed with water and dried (with anhydrous MgSO$_4$). Then, the solvent was removed by distillation to give a colorless transparent oil. To this were added 1.98 g of nitroiminoimidazolidine and 20 ml of DMF. Then, one ml of concentrated hydrochloric acid was added thereto at 80° C. and stirred for one hour at the same temperature. Water was added to the reaction mixture, which was then extracted with ethyl acetate, washed with water and dried (with anhydrous MgSO$_4$). Then, the solvent was removed by distillation to give a solid, which was sludged with ether to give 0.73 g of pale yellow crystals of 1-{2-(3-cyanophenyl)vinyl}-2-nitroiminoimidazolidine.

EXAMPLE 17 (INTERMEDIATE NO. 27)

A mixture comprising 4.0 g of 2-nitroiminoimidazolidine, 20 ml of 1,3-dimethyl-2imidazolidine, 7.5 g of phosphorus oxychloride and 2.7 g of propionaldehyde was stirred for 30 minutes at room temperature. The reaction mixture was poured into water, extracted with ethyl acetate, washed with water, dried (with anhydrous MgSO4) and concentrated. The crystals thus precipitated out were sludged with ethyl acetate, filtrated and dried to give 1.7 g of 1-(1-propenyl)-2-nitroiminoimidazolidine.

EXAMPLE 18 (INTERMEDIATE NO. 35)

A mixture comprising 8.1 g of 2-phenoxyethanol, 12.6 g of pyridinium chlorochromate and 100 ml of methylene chloride was stirred for 1.5 hours with ice-cooling and then for 4 hours at room temperature. The reaction mixture was subjected to decantation, and the solvent was removed by distillation to give 10.6 g of an oily residue. To this were added 5.1 g of nitroiminoimidazolidine, 0.07 g of boron trifluoride ether complex and 30 ml of 1,3-dimethyl-2-imidazolidinone, and the whole was stirred for one hour at 100° C. The reaction mixture was poured into water, extracted with ethyl acetate, washed with water, dried (with anhydrous MgSO4) and concentrated to give an oily residue. This was purified by column chromatography (silica gel, eluent: ethl acetate) to give 0.28 g of 1-(2-phenoxyvinyl)-2nitroiminoimidazolidine.

EXAMPLE 19 (INTERMEDIATE NO. 38)

A mixture comprising 8.4 g of 2-nitroimidazolidine, 70 ml of 1,3-dimethyl-2-imidazolidinone, 14.2 g of phosphorus oxychloride and 20.3 g of 1,1,3,3-tetraethoxypropane was stirred at 70° C. for 2.5 hours. The reaction mixture was poured into water, extracted with ethyl acetate, washed with water, dried (with anhydrous MgSO4) and concentrated to give an oily residue. This was purified by column chromatography (silica gel, eluent: ethyl acetate/hexane=2/1) to give 2.5 g of 1-(2-formylvinyl)-2-nitroiminoimidazolidine.

EXAMPLE 20 (INTERMEDIATE NO. 40)

A mixture comprising 10.0 g of 2-ethylthioethanol, 24.4 g of pyridinium chlorochromate and 100 ml of methylene chloride was stirred for 2 hours with cooling with ice. The reaction mixture was subjected to decantation to separate a methylene chloride layer, to which were added 12.3 g of nitroiminoimidazolidine, 14.5 g of phosphorus oxychloride and 11.0 g of 1.3-dimethyl-2-imidazolidinone and heated under reflux for 2 hours. The reaction mixture was poured into water, extracted with ethyl acetate, washed with water, dried (with anhydrous MgSO4) and concentrated to give an oily residue. This was purified by column chromatography (silica gel, eluent:ethyl acetate/hexane=3/1) to give 2.3 g of 1-(2-ethylthiovinyl)-2-nitroiminoimidazolidine.

EXAMPLE 21 (INTERMEDIATE NO. 43)

A mixture comprising 4.0 g of 2-nitroiminoimidazolidine, 4.7 g of 2-ethylhexylaldehyde, 0.05 g of boron trifluoride ether complex and 20 ml of 1,3-dimethyl-2-imidazolidinone was stirred at 120° C. for 3 hours. The reaction mixture was poured into water, extracted with ethyl acetate, washed with water, dried (with anhydrous MgSO4) and concentrated. The crystals thus precipitated out were sludged with ethyl acetate, filtrated and dried to give 1.7 g of 1-(2-ethyl-1-hexenyl)-2-nitroiminoimidazolidine.

EXAMPLE 22 (INTERMEDIATE NO. 27)

5.0 g of 2-nitroiminoimidazolidine and 4.5 g of propionaldehyde were dissolved in 25 ml of N,N-dimethylformamide, and 4.0 g of phosphorus pentoxide was added thereto with cooling with ice over a period of 20 minutes and thereafter stirred for 10 minutes at 10° C. 20 ml of water and 20 ml of ethyl acetate were added to the reaction mixture, and the crystals thus precipitated out were filtrated and dried to give 4.3 g of 1-(1-propenyl)-2-nitroiminoimidazolidine.

EXAMPLE 23 (INTERMEDIATE NO. 32)

2.0 g of 2-nitroiminoimidazolidine and 3.4 g of n-decylaldehyde were dissolved in 20 ml of N,N-dimethylimidazolidinone, and 2.8 g of phosphorus oxychloride was added thereto at room temperature over a period of 20 minutes and thereafter stirred for 10 minutes at 50° C. water was poured into the reaction mixture, which was then extracted with ethyl acetate, washed with water, dried with anhydrous sodium sulfate and concentrated to give 2.1 g of an oily product of 1-(1-n-decenyl)-2-nitroiminoimidazolidine.

EXAMPLE 24 (INTERMEDIATE NO. 27)

4.0 g of 2-nitroiminoimidaozlidine, 3.0 g of propionaldehyde, 6.0 g of acetic anhydride and 0.1 g of potassium hydrogensulfate were dissolved in 15 ml of N,N-dimethylformamide and stirred at 60° C. for 2 hours. 10 ml of ethyl acetate and 20 ml of hexane were added to the reaction mixture and stirred for 30 minutes. The crystals thus precipitated out were filtrated, washed with ethyl acetate and dried to give 3.5 g of 1-(1-propenyl)-2-nitroiminoimidazoliine.

In the same manner as in the preceding Examples 13 to 24, other compounds of the formula (2) were prepared and shown in Table 3 below.

TABLE 3

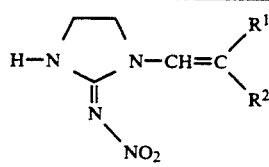

(2)

| Intermediate Compound No. | $R^1$ | $R^2$ | Value of Physical Properties |
|---|---|---|---|
| 1 | H | Ph | $\delta_{TMS}(CDCl_3)(ppm)$:3.95(4H, broad-s), 5.84(1H, d, J=14.7Hz), 7.18~7.36(5H, m), 7.58 (1H, d, J=14.7Hz), 8.46(1H, broad-s) <br> $\nu_{max}(KBr)(cm^{-1})$:3429, 1685, 1649, 1570, 1523, 1444, 1293, 1257, 1047, 932 |

TABLE 3-continued

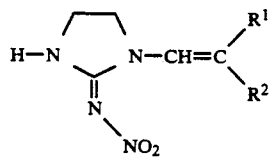

(2)

| Intermediate Compound No. | R¹ | R² | Value of Physical Properties |
|---|---|---|---|
| 2 | H | 2-CH₃—Ph | m.p.:140~145° C.<br>$\delta_{TMS}$(CDCl₃)(ppm):2.32(3H, s), 3.97(4H, s), 5.97(1H, d, J=14.7Hz), 7.12~7.17(3H, m), 7.43 (1H, d, J=6.6Hz), 7.47(1H, d, J=14.7Hz), 8.42(1H, s)<br>$\nu_{MAX}$(neat)(cm⁻¹):3434, 1646, 1582, 1531, 1486, 1469, 1428, 1345, 1298, 1220, 1143, 1051, 976, 934, 824, 784, 748, 716, 705. |
| 3 | H | 3-CH₃—Ph | m.p.:181.0~183.6° C.<br>$\delta_{TMS}$(DMSO-d₆)(ppm):2.30(3H, s), 3.76~3.81(2H, m), 3.85~3.89(2H, m), 5.93(1H, d, J=14.7Hz), 6.98(1H, d, J=7.3Hz), 7.13~7.20(3H, m), 7.39(1H, d, J=14.7Hz), 9.44(1H, broad-s)<br>$\nu_{MAX}$(KBr)(cm⁻¹):3419, 1648, 1582, 1526, 1443, 1295, 1220, 1140, 1050, 975, 935 |
| 4 | H | 4-CH₃—Ph | m.p.:197.3~197.7° C.(dec.)<br>$\delta_{TMS}$(CDCl₃)(ppm):2.33(3H, s), 3.95(4H, s), 5.81(1H, d, J=14.7Hz), 7.11(2H, d, J=8.1Hz), 7.24(2H, d, J=8.1Hz), 7.53(1H, d, J=14.7Hz), 8.40(1H, broad-s)<br>$\nu_{MAX}$(KBr)(cm⁻¹):3411, 1648, 1583, 1528, 1510, 1473, 1443, 1339, 1305, 1226, 1141, 1050, 974, 947 m.p.:163.6~164.2° C. |
| 5 | H | 4-tert-Bu—Ph | $\delta_{TMS}$(CDCl₃)(ppm):1.31(9H, s), 3.94(4H, s), 5.82(1H, d, J=14.7Hz), 7.28(2H, d, J=8.8Hz), 7.32(2H, d, J=8.8Hz), 7.54(1H, d, J=14.7Hz), 8.41(1H, s)<br>$\nu_{MAX}$(neat)(cm⁻¹):3382, 2959, 1650, 1601, 1527, 1480, 1444, 1290, 1219, 1142, 1047, 959 m.p.:170.3~172.6° C. |
| 6 | H | 4-CH₃O—Ph | $\delta_{TMS}$(CDCl₃)(ppm):3.79(3H, s), 3.90(4H, broad-s), 5.79(1H, d, J=14.7Hz), 6.82(2H, d, $J_{AB}$=8.8Hz), 7.26(2H, d, $J_{AB}$=8.8Hz), 7.41(1H, d, J=14.7Hz), 8.97(1H, broad-s)<br>$\delta_{MAX}$(KBr)(cm⁻¹):3417, 1646, 1592, 1532, 1441, 1306, 1243, 1141, 1046, 1027, 941, 840 m.p.:151~155° C. |
| 7 | H | 3,4-OCH₂O—Ph | $\delta_{TMS}$(CDCl₃)(ppm):3.94(4H, s), 5.77(1H, d, J=14.7Hz), 5.95(2H, s), 6.73(1H, d, J=6.6Hz), 6.76(1H, d, J=6.6Hz), 6.89(1H, s), 7.42, (1H, d, J=14.7Hz), 8.39(1H, broad-s)<br>$\nu_{MAX}$(KBr)(cm⁻¹):3415, 1643, 1592, 1533, 1501, 1444, 1380, 1362, 1296, 1252, 1145, 1038, 974, 924, 867, 832 |
| 8 | H | 4-CF₃OPh | m.p.:151~155° C.<br>$\delta_{TMS}$(CDCl₃)(ppm):3.96(4H, s), 5.81(1H, d, J=14.7Hz), 7.14(2H, d, J=8.1Hz), 7.35 (2H, d, J=8.8Hz), 7.55(1H, d, J=14.7Hz), 8.47(1H, broad-s)<br>$\nu_{MAX}$(KBr)(cm⁻¹):3366, 1649, 1590, 1525, 1508, 1450, 1314, 1259, 1219, 1196, 1148, 1053, 941, 849 m.p.:150.7~152.6° C. |
| 9 | H | 4-CF₃CH₂O—Ph | $\delta_{TMS}$(DMSO-d₆)(ppm):3.76~3.80(2H, m), 3.84~3.89(2H, m), 4.72(2H, q, J=8.8Hz), 5.95(1H, d, J=14.7Hz), 6.99(2H, d, J=8.8Hz), 7.32(1H, d, J=14.7Hz), 7.35 (2H, d, J=8.8Hz), 9.41(1H, broad-s)<br>$\nu_{MAX}$(KBr)(cm⁻¹):3382, 1650, 1589, 1510, 1445, 1291, 1238, 1161, 1076, 975, 844 m.p.136.0~147.1° C. |
| 10 | H | 2,4-(CH₃)Ph | $\delta_{TMS}$(CDCl₃)(ppm):2.28(3H, s), 2.30(3H, s), 3.97(4H, s), 5.95(1H, d, J=14.7Hz), 6.97(1H, d, J=8.1Hz), 7.26(1H, s), 7.33(1H, d, J=8.1Hz), 7.44(1H, d, J=14.7Hz), 8.41(1H, broad-s)<br>$\nu_{MAX}$(KBr)(cm⁻¹):3419, 1640, 1587, 1524, 1473, 1438, 1296, 1226, 1142, 1049, 974, 940, 833 m.p.:188.9~190.1° C. |
| 11 | H | 2,5-(CH₃)Ph | $\delta_{TMS}$(CDCl₃)(ppm):2.27(3H, s), 2.31(3H, s), 3.95(4H, s), 5.94(1H, d, J=14.7Hz), 6.93(1H, d, J=7.3Hz), 7.01(1H, d, J=7.3Hz), 7.26(1H, s), 7.45(1H, d, J=14.7Hz), 8.43(1H, broad-s)<br>$\nu_{MAX}$(KBr)(cm⁻¹):3409, 1648, 1592, 1526, 1473, 1443, 1376, 1343, 1224, 1143, 1106, 1047, 962, 937, 820 m.p.:159.4~160.4° C. |
| 12 | H | 3,4-(CH₃)Ph | $\delta_{TMS}$(CDCl₃)(ppm):2.22(3H, s), 2.24(3H, s), 3.89~3.93(4H, m), 5.85(1H, d, J=14.7Hz), 7.00~7.12(3H, m), 7.43(1H, d, J=14.7Hz), 9.33(1H, broad-s)<br>$\nu_{MAX}$(KBr)(cm⁻¹): 3423, 1649, 1583, 1530, 1440, 1297, 1141, 1048, 933, 783 m.p.:224~232° C.(dec.) |
| 13 | H | 2-Cl—Ph | $\delta_{TMS}$(CDCl₃)(ppm):3.93(4H, broad-s), 5.78(1H, d, J=14.7Hz), 7.12~7.33(4H, m), 7.55(1H, d, J=14.7Hz), 9.25(1H, broad-s)<br>$\nu_{MAX}$(KBr)(cm⁻¹):3367, 1641, 1579, 1520, 1444, 1285, 1210, 1048, 966, 937 m.p.:201~203° C. |
| 14 | H | 3-Cl—Ph | $\delta_{TMS}$(CDCl₃)(ppm):3.98~4.02(4H, m), 6.19(1H, d, J=14.7Hz), 7.13~7.56(4H, m), 7.57(1H, d, J=14.7Hz), 8.46(1H, broad-s)<br>$\nu_{MAX}$(KBr)(cm⁻¹):3403, 1649, 1579, 1531, 1442, 1298, 1233, 1048, 936, 802 m.p.:203~204.5° C. |
| 15 | H | 4-Cl—Ph | $\delta_{TMS}$(CDCl₃)(ppm):3.93(4H, broad-s), 5.78(1H, d, J=14.7Hz), 7.25(2H, d, $J_{AB}$=6.6Hz), 7.28(2H, d, $J_{AB}$=6.6Hz)7.54(1H, d, J=14.7Hz), 8.94(1H, broad-s)<br>$\nu_{MAX}$(KBr)(cm⁻¹):3421, 1650, 1586, 1523, 1434, 1298, 1229, 1142, 1048, 975, 935, 843 m.p.:165~169° C. |
| 16 | H | 4-F—Ph | $\delta_{TMS}$(DMSO-d₆)(ppm):3.78~3.81(2H, m), 3.84~3.87(2H, m), 6.00(1H, d, J=14.7Hz), 7.12(2H, t, J=8.8Hz), 7.36(1H, d, J=14.7Hz), 7.39~7.43(2H, m), 9.44(1H, broad-s)<br>$\nu_{MAX}$(KBr)(cm⁻¹):3418, 1653, 1588, 1527, 1507, 1441, 1301, 1227, 1140, 1045, 949 m.p.193.2~194.0° C.(dec.) |
| 17 | H | 2,3-Cl₂—Ph | $\delta_{TMS}$(DMSO-d₆)(ppm):3.80~3.84(2H, m), 3.90~3.95(2H, m), 6.10(1H, d, J=14.7Hz), 7.31(1H, t, J=8.1Hz), 7.45(1H, dd, J=8.1Hz, J=1.5Hz), 7.51(1H, d, J=14.7Hz), 7.60~7.62(1H, m), 9.61(1H, broad-s)<br>$\nu_{MAX}$(KBr)(cm⁻¹):3366, 1640, 1576, 1524, 1439, 1284, 1139, 937, 774 m.p.214.6~215.0° C.(dec.) |

TABLE 3-continued $$\text{H-N} \overset{\underset{\displaystyle\|}{\text{N}}\atop\underset{\displaystyle\text{NO}_2}{}}{\overset{\frown}{\text{N}}}\text{—CH}=\text{C}\overset{R^1}{\underset{R^2}{}}\quad(2)$$

| Intermediate Compound No. | R¹ | R² | Value of Physical Properties |
|---|---|---|---|
| 18 | H | 2,4-Cl₂—Ph | δ$_{TMS}$(DMSO-d₆)(ppm):3.80~3.82(2H, m), 3.89~3.91(2H, m), 6.00(1H, d, J=14.7Hz), 7.33(1H, d, J=2.2Hz), 7.34(1H, dd, J=8.8Hz, J=2.2Hz), 7.50(1H, d, J=14.7Hz), 7.56 (1H, d, J=2.2Hz), 7.65(1H, d, J=8.1Hz), 9.58(1H, broad-s)<br>ν$_{MAX}$(KBr)(cm⁻¹):3417, 1644, 1587, 1522, 1474, 1439, 1292, 1239, 1140, 1047, 962, 869, 834, 750 m.p.221.3~222.5° C.(dec.) |
| 19 | H | 2,6-Cl₂—Ph | δ$_{TMS}$(DMSO-d₆)(ppm):3.83~3.85(2H, m), 3.90~3.92(2H, m), 5.83(1H, d, J=14.7Hz), 7.24(1H, t, J=8.1Hz), 7.49(2H, d, J=8.1Hz), 7.56(1H, d, J=14.7Hz), 9.59(1Hbroad-s)<br>ν$_{MAX}$(KBr)(cm⁻¹):3397, 1638, 1589, 1525, 1453, 1436, 1292, 1211, 1140, 1050, 965, 945, 769 m.p.204.3~205.9° C.(dec.) |
| 20 | H | 3,4-Cl₂—Ph | δ$_{TMS}$(DMSO-d₆)(ppm):3.79~3.86(4H, m), 5.96(1H, d, J=14.7Hz), 7.39(1H, dd, J=8.1Hz, J=2.2Hz), 7.49(1H, d, J=14.7Hz), 7.50(1H, d, J=8.8Hz), 7.63(1H, d, J=2.2Hz), 9.53(1H, broad-s)<br>ν$_{MAX}$(KBr)(cm⁻¹):3415, 1647, 1586, 1525, 1474, 1440, 1293, 1229, 1133, 1048, 937 m.p.252.6~253.3° C.(dec.) |
| 21 | H | 3-CN—Ph | δ$_{TMS}$(DMSO-d₆)(ppm):3.81~3.83(2H, m), 3.85~3.88(2H, m), 6.01(1H, d, J=14.7Hz), 7.50(1H, t, J=8.1Hz), 7.56(1H, d, J=14.7Hz), 7.58~7.60(1H, m), 7.73(1H, d, J=8.1Hz), 7.87(1H, s), 9.55(1H, broad-s)<br>ν$_{MAX}$(KBr)(cm⁻¹):3397, 2227, 1648, 1578, 1526, 1446, 1305, 1223, 1047, 947 m.p.230.5~232.2° C. |
| 22 | CH₃ | Ph | δ$_{TMS}$(CDCl₃)(ppm):2.14(3H, s), 3.87~4.00(4H, m), 6.55(1H, s), 7.25~7.39(5H, m), 8.33(1H, broad-s)<br>ν$_{MAX}$(KBr)(cm⁻¹):3334, 1644, 1579, 1522, 1445, 1289, 1244, 1052, 967, 771 m.p.:167~168° C. |
| 23 | H | CH₃Ph | δ$_{TMS}$(DMSO₆)(ppm):3.34~3.57(2H, m), 3.70(2H, s), 5.08~5.11(1H, m), 6.81(1H, d, J=13.9Hz), 7.19~7.31(5H, m), 9.25(1H, s)<br>ν$_{MAX}$(KBr)(cm⁻¹):3361, 1662, 1576, 1523, 1493, 1469, 1444, 1345, 1217, 1141, 1076, 1042, 962, 784, 754, 702 m.p.:143~146° C. |
| 24 | Ph | Ph | δ$_{TMS}$(CDCl₃)(ppm):3.21~3.25(2H, m), 3.63~3.67(2H, m), 7.14~7.18(2H, m), 7.25~7.27(6H, m), 7.37~7.40(3H, m), 8.30(12H, s)<br>ν$_{MAX}$(neat)(cm⁻¹):3400, 1633, 1591, 1518, 1493, 1473, 1436, 1295, 1240, 1133, 1051, 974, 942, 762, 748, 702 m.p.:153.8~155.2° C. |
| 25 | H | Ph—Ph | δ$_{TMS}$(DMSO-d₆)(ppm):3.78~3.82(2H, m), 3.88~3.93(2H, m), 6.03(1H, d, J=14.7Hz), 7.34(1H, t, J=7.3Hz), 7.43~7.50(5H, m), 7.61~7.67(4H, m), 9.48(1H, s) |
| 26 | H | PhCOPh | δ$_{TMS}$(CDCl₃)(ppm):3.82~3.84(2H, m), 3.89~3.92(2H, m), 6.06(1H, d, J=14.7Hz), 7.52~7.72(10H, m), 79.56(1H, broad-s) |
| 27 | H | CH₃ | δ$_{TMS}$(DMSO-d₆)(ppm):1.69(3H, dd, J=6.6Hz, J=1.5Hz), 3.65~3.75(4H, m), 4.92(1H, qd, J=13.9Hz, J=6.6Hz), 6.69(1H, dd, J=1.5Hz, J=13.9Hz), 9.19(1H, broad-s)<br>ν$_{MAX}$(KBr)(cm⁻¹):3348, 1671, 1589, 1535, 1436, 1387, 1310, 1230, 1159, 1048, 965 m.p.:164.5~166.0° C. |
| 28 | CH₃ | CH₃ | δ$_{TMS}$(CDCl₃)(ppm):1.72(3H, d, J=1.5Hz), 1.75(3H, d, J=1.5Hz), 3.78~3.85(4H, m), 5.91(1H, d, J=1.5Hz), 8.23(1H, broad-s)<br>ν$_{MAX}$(KBr)(cm⁻¹):3352, 1679, 1588, 1524, 1434, 1382, 1315, 1225, 1133, 1057 m.p.:136.6~138.8° C. |
| 29 | H | iso-C₃H₇ | δ$_{TMS}$(CDCl₃)(ppm):1.03(6H, d, J=7.3Hz), 2.33~2.42(1H, m), 3.75~3.92(4H, m), 4.87(1H, dd, J=13.9Hz, J=7.3Hz), 6.82(1H, d, J=13.9Hz), 8.34(1H, broad-s) |
| 30 | H | n-C₄H₉ | δ$_{TMS}$(CDCl₃)(ppm):0.90(3H, t, J=6.6Hz), 1.24~1.40(4H, m), 2.04~2.09(2H, m), 3.76~3.92(4H, m), 4.90(1H, d, t, J=14.0Hz, J=6.6Hz), 6.86(1H, d, J=14.0Hz) 8.31(1H, broad-s)<br>ν$_{MAX}$(KBr)(cm⁻¹):3347, 1667, 1578, 1531, 1456, 1292, 1243, 1048, 968 m.p.:78~81° C. |
| 31 | H | n-C₆H₁₃ | δ$_{TMS}$(CDCl₃)(ppm):0.88(3H, t, J=7.3Hz), 1.21~1.38(8H, m), 2.03~2.08(2H, m), 3.76~3.81(2H, m), 3.87~3.92(2H, m), 4.87~4.94(1H, m), 6.85(1H, d, J=13.9Hz), 8.31(1H, broad-s)<br>ν$_{MAX}$(KBr)(cm⁻¹):3428, 1664, 1594, 1530, 1427, 1307, 1241, 1112, 1046, 948 m.p.:62~65° C. |
| 32 | H | n-C₈H₁₇ | δ$_{TMS}$(CDCl₃)(ppm):0.86~0.90(3H, m), 1.26~1.30(10H, m), 1.54~1.57(2H, m), 3.32~3.36(2H, m), 3.60~3.65(2H, m), 3.77~3.81(2H, m), 8.09(1H, s) |
| 33 | H | n-C₁₀H₂₁ | δ$_{TMS}$(CDCl₃)(ppm):0.88(3H, t, J=7.3Hz), 1.13~1.46(12H, m), 2.05(2H, dt, J=7.3Hz, J=7.3Hz), 3.76~3.91(4H, m), 4.89(1H, dt, J=7.3Hz, J=14.7Hz), 6.86(1H, d, J=14.7Hz), 8.29(1H, broad-s)<br>ν$_{MAX}$(KBr)(cm⁻¹):3439, 2916, 2850, 1666, 1586, 1537, 1438, 1293, 1217, 1112, 1046, 951 m.p.:71.0~73.0° C. |
| 34 | H | OCH₃ | δ$_{TMS}$(CDCl₃):3.64(3H, s), 3.79~3.84(2H, m), 4.09~4.14(2H, m), 5.57) 1H, d, J=5.9Hz), 5.75(1H, d, J=5.9Hz), 8.17(1H, broad-s)<br>ν$_{MAX}$(KBr)(cm⁻¹):3365, 1577, 1537, 1441, 1296, 1212, 1054, 951 m.p.:147.0~150.5° C. |
| 35 | H | OPh | δ$_{TMS}$(DMSO-d₆)(ppm):3.77~3.82(2H, m), 3.90~3.95(2H, m), 6.39(1H, d, J=11.0Hz), 6.99(1H, d, J=8.1Hz), 7.06(1H, t, J=8.1Hz), 7.12(1H, d, J=11.0Hz), 7.32 (2H, t, J=8.1Hz), 8.82(1H, broad-s)<br>ν$_{MAX}$(KBr)(cm⁻¹):3340, 1583, 1531, 1439, 1286, 1215, 1048, 917, 755 |
| 36 | CH₃ | CF₃ | δ$_{TMS}$(CDCl₃)(ppm):1.09(2/5*3H, d, J=7.3Hz), 1.25(3/5*3H, d, J=6.6Hz), 3.71~ |

TABLE 3-continued

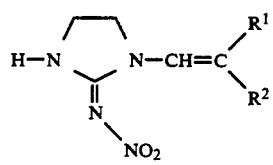

(2)

| Intermediate Compound No. | R¹ | R² | Value of Physical Properties |
|---|---|---|---|
| | | | 3.87(4H, m), 5.54~5.60(1H, m), 8.76(3/5*1H, broard-s), 8.83(2/5*1H, broard-s) |
| | | | $\nu_{MAX}$(KBr)(cm$^{-1}$):3374, 1583, 1535, 1446, 1294, 1263, 1141, 1043, 975 |
| | | | m.p.:115° C.(dec.) |
| 37 | H | n-C$_4$F$_9$ | $\delta_{TMS}$(CDCl$_3$)(ppm):3.83~3.89(2H, m), 4.00~4.04(2H, m), 4.88(1H, q, J=11.9Hz), |
| | | | 7.67(1H, d, J=13.9Hz), 8.58(1H, broad-s) |
| | | | $\nu_{MAX}$(KBr)(cm$^{-1}$):3326, 1699, 1605, 1527, 1487, 1450, 1300, 1236, 1051, 960, 885, 822 |
| | | | m.p.:124~129.5° C. |
| 38 | H | CHO | $\delta_{TMS}$(DMSO-d$_6$)(ppm):3.92~4.02(4H, m), 5.59(1H, dd, J=13.9Hz, J=7.3Hz), |
| | | | 7.96(1H, d, J=13.9Hz), 9.52(1H, d, J=8.1Hz), 9.81(1H, broad-s) |
| | | | $\nu_{MAX}$(KBr)(cm$^{-1}$):3358, 1595, 1514, 1449, 1313, 1228, 1167, 1112, 964, 748 |
| | | | m.p.:143.5~145.5° C.dec. |
| 39 | H | NHCOPh | $\delta_{TMS}$(acetone-d$_6$)(ppm):3.82~3.90(4H, m), 6.74(1H, dd, J=13.2Hz, J=9.5Hz), |
| | | | 7.31(1H, d, J=13.2Hz), 7.42~7.51(3H, m), 7.96(2H, d, J=6.6Hz), 8.90(1H, broad-s), |
| | | | 10, 12(1H, d, J=9.5Hz) |
| | | | $\nu_{MAX}$(KBr)(cm$^{-1}$):3389, 1617, 1574, 1529, 1439, 1283, 1227, 1055, 921 |
| | | | m.p.:254~255(dec.) |
| 40 | H | SC$_2$H$_5$ | $\delta_{TMS}$(CDCl$_3$)(ppm):1.27(3H, t, J=7.3Hz), 2.64(2H, q, J=7.3Hz), 3.81~3.95 |
| | | | (4H, m), 5.43(1H, d, J=13.2Hz), 7.15(1H, d, J=13.2Hz), 8.40(1H, broad-s) |
| | | | $\nu_{MAX}$(neat)(cm$^{-1}$):3396, 2969, 2927, 1579, 1524, 1443, 1292, 1235, 1139, 1045, 967 |
| 41 | H | 2-Cl-pyridin-5-yl | $\delta_{TMS}$(CDCl$_3$)(ppm):3.79~3.91(4H, m), 6.00(1H, d, J=14.7Hz), 7.40(1H, d, J=8.8Hz), |
| | | | 7.53(1H, d, J=14.7Hz), 7.94(1H, dd, J=8.8Hz, J=2.9Hz), 8.38(1H, d, J=2.9Hz), |
| | | | 8.99(1H, broad-s) |
| | | | $\nu_{MAX}$(KBr)(cm$^{-1}$):3414, 1648, 1578, 1515, 1430, 1298, 1222, 1050, 951 |
| | | | m.p.:210~213(dec.)°C. |
| 42 | H | 4-CH$_3$S—Ph | $\delta_{TMS}$(CDCl$_3$)(ppm):2.49(3H, s), 3.95(4H, s), 5.79(1H, d, J=14.7Hz), 7.19 |
| | | | (2H, d, J=8.1Hz), 7.27(2H, d, J=8.1Hz), 7.55(1H, d, J=14.7Hz), 8.41(1H, broad-s) |
| | | | $\nu_{MAX}$(KBr)(cm$^{-1}$):3402, 1643, 1595, 1523, 1442, 1300, 1215, 1143, 1046, 938 |
| | | | m.p.:201.7~202.4° C. |
| 43 | C$_2$H$_5$ | n-C$_4$H$_9$ | $\delta_{TMS}$(CDCl$_3$)(ppm):0.89~0.93(3H, m), 1.01~1.07(3H, m), 1.26~1.55(4H, m), |
| | | | 1.99~2.18(4H, m), 3.69~3.85(4H, m), 6.01(1H, s), 8.10(1H, broad-s) |

Next, preparation of intermediates of the formula (7) is mentioned below by way of the following example.

EXAMPLE 25

A mixture comprising of 25 g of 2-nitroiminoimidazolidine, 100 g of ethyl orthoformate and 25 ml of 1,3-dimetyl-2-imidazolidinone was heated under reflux for 3 hours. After cooled to room temperature, the reaction mixture was poured into water and extracted with ethyl acetate. After washed with water and dried (with anhydrous magnesium sulfate), the solvent was removed by distillation under reduced pressure. The crystals thus obtained were sludged with ether to give 32 g of 1-diethoxymethyl-2-nitroiminoimidaozlidine.

| | |
|---|---|
| $\delta_{TMS}$(CDCl$_3$)(ppm): | 1.24(6H, t, J=6.9Hz), |
| | 3.44 to 3.87(8H, m), |
| | 5.95(1H, s), 8.36(1H, s) |
| $\nu_{MAX}$(KBr)(cm-1): | 3340, 1570, 1530, 1470, |
| | 1440, 1280, 1220, 1170, |
| | 1090, 1040, 1010 |
| m.p.: 100.2 to 101.8° C. | |

Next, the compositions of the present invention are more particularly described by way of the following formulation examples, in which all "parts" are "parts by weight".

FORMULATION EXAMPLE 1

20 parts of the compound of the invention, 10 parts of Sorpol 355S (surfactant available from Toho Chem. Co.) and 70 parts of xylene were uniformly stirred and mixed to give an emulsion.

FORMULATION EXAMPLE 2

10 parts of the compound of the invention, 2 parts of sodium alkylnaphthalenesulfonate, 5 parts of white carbon and 82 parts of diatomaceous earth were uniformly stirred and mixed to give 100 parts of a wettable powder.

FORMULATION EXAMPLE 3

0 3 part of the compound of the invention and 0.3 part of white carbon were uniformly mixed, and 99.2 parts of clay and 0.2 part of Driless A (available from Sankyo Co.) were added thereto and uniformly ground and mixed to give 100 parts of a powder preparation.

FORMULATION EXAMPLE 4

2 parts of the compound of the invention, 2 parts of white carbon, 2 parts of sodium ligninsulfonate and 94 parts of bentonite were uniformly ground and mixed, and water was added thereto and kneaded, granulated and dried to give 100 parts of a granular preparation.

FORMULATION EXAMPLE 5

20 parts of the compound of the invention and 5 parts of 20 % aqueous solution of polyvinyl alcohol were fully stirred and mixed, and 75 parts of 0.8 % aqueous solution of xanthane gum was added thereto and again stirred and mixed to give 100 parts of a flowable preparation.

FORMULATION EXAMPLE 6

10 parts of the compound of the invention, 3 parts of carboxymethyl cellulose, 2 parts of sodium ligninsulfonate, one part of sodium diocytlsulfosuccinate and 84 parts of water were uniformly wet-ground to give 100 parts of a flowable preparation.

The insecticidal activity of the compounds of the formula (1) of the invention is clarified by way of the following test examples.

TEST EXAMPLE 1

Effect on *Laodelphax sriatellus* Fallen—smaller brown planthopper

The emulsion prepared in Formulation Example 1 was diluted to a predetermined concentration and 2 ml of the diluted emulsion was applied over a bundle of several rice seedlings (about third leaf stage). After drying in air, the treated seedlings were covered with a metal gauze cylinder, in which ten female adults of the smaller brown planthopper were released, followed by placing in a temperature controlled room at 25° C. After 48 hours, the mortality was checked. The results are shown in Table 3.

TABLE 3

| Effect on *Laodelphax striatellus* Fallen - smaller brown planthopper | |
|---|---|
| Test Compound | Mortality (%) 5 ppm |
| Nos. 1, 3 to 9, 11, 12, 14, 16 to 18, 20 to 32, 33, 35 to 38, 40, 41, 42 | 100 |
| Reference Chemical (1) | 20 |
| Reference Chemical (2) | 20 |

Reference Chemical (1): 1-(2-chloropyridin-5-ylmethyl)-2-nitroimino-3-{2-(4-chlorophenyl)ethyl}imidazolidine
Reference Chemical (2): 1-(2-chloropyridin-5-ylmethyl)-2-nitroimino-3-methoxymethylimidazolidine

TEST EXAMPLE 2

Effect on resistant strain of *Nephotettix cincticeptus* Uhler—resistant green rice leafhopper The emulsion prepared in Formulation Example 1 was diluted to a predetermined concentration and 3 ml of the diluted emulsion was applied over a bundle of several rice seedlings (about third leaf stage). After drying in air, the treated seedlings were covered with a metal gauze cylinder, in which ten female adults of the leafhopper that is resistant to organophosphate and carbamate insecticides were released, followed by placing in a temperature controlled room at 25° C. After 48 hours, the mortality was checked. The results are shown in Table 4.

TABLE 4

| Effect on resistant strain of *Nephotettix cincticeptus* Uhler - resistant green rice leafhopper | |
|---|---|
| Test Compound | Mortality (%) 3 ppm |
| Nos. 1, 2, 3 to 8, 10, 11, 14 to 32, 33, 35 to 38, 40, 41 to 43 | 100 |
| Reference Chemical (1) | 25 |
| Reference Chemical (2) | 30 |

Reference Chemical (1): 1-(2-chloropyridin-5-ylmethyl)-2-nitroimino-3-{2-(4-chlorophenyl)ethyl}imidazolidine
Reference Chemical (2): 1-(2-chloropyridin-5-ylmethyl)-2-nitroimino-3-methoxymethylimidazolidine

TEST EXAMPLE 3

Effect on *Callosobruchus chinensis* Linne—Azuki bean weevil:

An acetone solution of the compound of the invention was added to a Petri dish with a diameter of 9 cm, followed by removal of the acetone by evaporation. Twenty female adults of the Azuki bean weevil, which were 2 to 3 days after emergence were placed in the dish at 25° C. After 48 hours, the mortality was checked. The results are shown in Table 5.

TABLE 5

| Effect on *Callosobruchus chinensis* Linne - Azuki bean weevil | |
|---|---|
| Test Compound | Mortality (%) 0.01 mg/dish |
| Nos. 1 to 45 | 100 |
| Diazinone | 58 |

TEST EXAMPLE 4

Effect on *Myzus persicae* Suizer green peach aphid 20 ml of a dilution of the emulsion prepared in Formulation Example 1 was sprayed over potted eggplant seedlings (fourth or fifth leaf stage), as having been grown in a greenhouse, on which the green peach aphids had been parasitic. After the application, the seedlings were placed in the greenhouse and, after three days, the number of the aphids was checked. The results are shown in Table 6.

TABLE 6

| Effect on *Myzus persicae* Suizer - green peach aphid | | |
|---|---|---|
| Test Compound | Concentration | Density of Living Insects |
| Nos. 1 to 45 | 50 ppm | 0 to 2 |
| DDVP | 50 ppm | 30 |
| Non treated | — | 130 |

Density of Living Insects = 100 × (number of living insects after treatment/number of living insects before treatment)

TEST EXAMPLE 5

Effect on *Laodelphax striatellus* Fallen—smaller brown planthopper

The emulsion prepared in Formulation Example 1 was diluted to predetermined concentrations, and 2 ml of each diluted emulsion was applied over a bundle of several rice seedlings (about third leaf stage). After drying in air, the treated seedlings were covered with a metal gauze cylinder, in which ten female adults of the smaller brown planthopper were released, followed by placing in a temperature controlled room at 25° C. After 48 hours, the mortality was checked, from which the medium-lethal concentration (LCO) was obtained. The results are shown in Table 7.

TEST EXAMPLE 6

Effect on resistant strain of *Nephotettix cincticeptus* Uhler—resistant green rice leafhopper The emulsion prepared in Formulation Example 1 was diluted to predetermined concentrations, and 2 ml of each diluted emulsion was applied over a bundle of several rice seedlings (about third leaf stage). After drying in air, the treated seedlings were covered with a metal gauze cylinder, in which ten female adults of the leafhopper that is resistant to organophosphate and carbamate insecticides were released, followed by placing in a temperature controlled room at 25° C. After 48 hours, the mortality was checked, from which the 50 %-lethal concentration (LC$_{50}$) was obtained. The results are shown in Table 7.

TEST EXAMPLE 7

Effect on *Myzus persicae* Suizer—green peach aphid

20ml of a 10ppm dilution of the emulsion prepared in Formulation Example 1 was sprayed over potted eggplant seedlings (fourth or fifth leaf stage), as having been grown in a greenhouse, on which the green peach aphids had been parasitic. After the application, the seedlings were placed in the greenhouse and, after three days, the number of the aphids was checked, from which the density of the living insects was obtained. The tests were repeated two times. The results are shown in Table 7.

TABLE 7

| Test Compound | Test Example 5 LC$_{50}$ (ppm) | Test Example 6 LC$_{50}$ (ppm) | Test Example 7 Density of Living Insects (1 ppm) |
|---|---|---|---|
| No. 27 | 1 | 0.3 | 0 |
| No. 2 | 3 | 1.5 | 20 |
| Reference Chemical 1 | 10 | 3 | 25 |
| Reference Chemical 2 | 20 | 10 | 108 |
| Non treated | — | — | 387 |

Density of Living Insects = 100 × (number of living insects after treatment/number of living insects before treatment)
Reference Chemical 1: 1-(2-chloropyridin-5-ylmethyl)-2-nitroimino-3-allylimidazolidine (described in U.S. Pat. No. 4,742,060)
Reference Chemical 2: 1-(2-chloropyridin-5-ylmethyl)-2-nitroimino-3-(2-phenylethyl)imidazolidine From these results, it is noted that the compounds of the invention have higher insecticidal activity than the known compounds of the prior art.

TEST EXAMPLE 8

Acute Toxicity Test to Mice

The compound of the invention having a predetermined concentration was dissolved in corn oil and applied to 6-week mice by forced peroral administration. Up to 14 days from the administration, the number of the died mice was counted periodically, from which the 50 %-lethal concentration (LD$_{50}$) was obtained. One group for the test comprised ten mice. The results are shown in Table 8.

TABLE 8

| Acute Toxicity to Mice | |
|---|---|
| Text Compound | LD$_{50}$ (mg/kg) |
| No. 27 | 1000 |
| No. 10 | >5000 |
| Reference Chemical 1 | 100 to 200 |

Reference Chemical 1: 1-(2-chloropyridin-5-ylmethyl)-2-nitroimino-3-allylimidazolidine (described in U.S. Pat. No. 4,742,060)

From the results of the test, it is understood that the compounds of the present invention are less toxic and are more safe than the known compound of the prior art.

EFFECT OF THE INVENTION

Novel N-vinylimidazolidine derivatgives of the formula (1) of the present invention are excellent compounds having a high insecticidal power and a broad insecticidal spectrum.

Novel N-vinylimidazolidine derivatgives of the formula (1) of the invention may be produced with ease from novel intermediates of the formula (2) in accordance with the process of the invention.

What is claimed is:

1. An N-vinylimidazolidine compound of the formula (1):

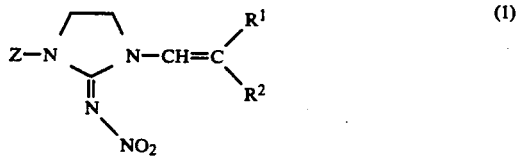

where R$^1$ represents a hydrogen atom, a phenyl group, or an alkyl group having from 1 to 4 carbon atoms; R$^2$ represents a hydrogen atom, a phenoxy group, a benzyl group, a phenyl group, a -C(=O)H group, a 2-chloropyridin-5 ylmethyl group, a benzoylamino group, an alkyl group having from 1 to 18 carbon atoms, an alkoxy group having from 1 to 4 carbon atoms, an alkylthio group having from 1 to 4 carbon atoms, a phenyl group substituted by halogen atom(s), a phenyl group substituted by cyano group(s), a phenyl group substituted by phenyl group(s), a phenyl group substituted by benzoyl group(s), a phenyl group substituted by methylenedioxy group(s), a phenyl group substituted by alkyl group(s) having from 1 to 4 carbon atoms, a phenyl group substituted by alkoxy group(s) having from 1 to 4 carbon atoms, a phenyl group substituted by alkylthio group(s) having from 1 to 4 carbon atoms, a phenyl group substituted by haloalkyl group(s) having from 1 to 4 carbon atoms, or a phenyl group substituted by haloalkoxy group(s) having from 1 to 4 carbon atoms; and Z represent a 2-chloropyridin-5-ylmethyl group or a 2 -chlorothiazol-5-ylmethyl group.

2. An N-vinylimidazolidine compound as claimed in claim 1, in which R$^2$ represents a hydrogen atom, a phenoxy group, a benzyl group, a phenyl group, group, -C(=O)H group, a 2-chloropyridin-5-ylmethyl group, or a benzoylamino group.

3. An N-vinylimidazolidine compound as claimed in claim 1, in which R$^2$ represents an alkyl group having from 1 to 18 carbon atoms.

4. An N-vinylimidazolidine compound as claimed in claim 1, in which R$^2$ represents a phenyl group substituted by halogen atom(s), a phenyl group substituted by cyano group(s), a phenyl group substituted by phenyl group(s), a phenyl group substituted by benzoyl group(s), a phenyl group substituted by methylenedioxy group(s), a phenyl group substituted by alkyl group(s) having from 1 to 4 carbon atoms, a phenyl group substituted by alkoxy group(s) having from 1 to 4 carbon atoms, a phenyl group substituted by alkylthio group(s) having from 1 to 4 carbon atoms, a phenyl group substituted by haloalkyl group(s) having from 1 to 4 carbon atoms, or a phenyl group substituted by haloalkoxy group(s) having from 1 to 4 carbon atoms.

5. An insecticide a carrier and, as an effective ingredient, a compound of claim 1 of the formula (1): a 2-chloropyridin-5-ylmethyl group or a 2-chlorothiazol-5ylmethyl group.

6. The insecticide as claimed in claim 5, in which R$^2$ represents a hydrogen atom, a phenoxy group, a benzyl group, a phenyl group, a -C(=O)H group, a 2-chloroyridin-5-ylmethyl group, or a benzoylamino group.

7. The insecticide as claimed in claim 5, in which $R^2$ represents an alkyl group having from 1 to 18 carbon atoms.

8. The insecticide as claimed in claim in claim 5, in which $R^2$ represents a phenyl group substituted by halogen atom(s), a phenyl group substituted by cyano group(s), a phenyl group substituted by phenyl group(s), a phenyl group substituted by benzoyl group(s), a phenyl group substituted by methylenedioxy group(s), a phenyl group substituted by alkyl group(s) having from 1 to 4 carbon atoms, a phenyl group substituted by alkoxy group(s) having from 1 to 4 carbon atoms, a phenyl group substituted by alkylthio group(s) having from 1 to 4 carbon atoms, a phenyl group substituted by haloalkyl group(s) having from 1 to 4 carbon atoms, or a phenyl group substituted by haloalkoxy group(s) having from 1 to 4 carbon atoms.

* * * * *